US011886772B2

(12) United States Patent
Atarot et al.

(10) Patent No.: US 11,886,772 B2
(45) Date of Patent: *Jan. 30, 2024

(54) VOCALLY ACTUATED SURGICAL CONTROL SYSTEM

(71) Applicant: Asensus Surgical Europe S.a.r.l, Lugano (CH)

(72) Inventors: Gal Atarot, Kfar Saba (IL); Motti Frimer, Zichron Yaakov (IL); Tal Nir, Haifa (IL); Lior Alpert, Haifa (IL)

(73) Assignee: Asensus Surgical Europe S.a.r.l, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,477

(22) Filed: Dec. 19, 2022

(65) Prior Publication Data
US 2023/0123443 A1 Apr. 20, 2023

Related U.S. Application Data

(60) Continuation of application No. 17/064,549, filed on Oct. 6, 2020, now Pat. No. 11,561,762, which is a
(Continued)

(51) Int. Cl.
*A61B 34/30* (2016.01)
*G06F 3/16* (2006.01)
(Continued)

(52) U.S. Cl.
CPC .............. *G06F 3/167* (2013.01); *A41D 13/11* (2013.01); *A61B 34/30* (2016.02); *G10L 15/22* (2013.01);
(Continued)

(58) Field of Classification Search
CPC .................... G06F 3/167; A61B 34/30; A61B 2017/00017; A61B 2017/00203; G10L 15/22
See application file for complete search history.

(56) References Cited

U.S. PATENT DOCUMENTS 4,559,928 A * 12/1985 Takayama ............ A61B 1/0052
600/152
4,854,301 A * 8/1989 Nakajima ............... A61B 90/50
600/102
(Continued)

FOREIGN PATENT DOCUMENTS

CN 112530430 A * 3/2021 ............ G10L 15/22
EP 2520993 A2 * 11/2012 ........... G05B 19/409
(Continued)

OTHER PUBLICATIONS

"Emotion sensitive speech control for human-robot interaction in minimal invasive surgery;" Schuller et al., The 17th IEEE International Symposium on Robot and Human Interactive Communication (pp. 453-458); Sep. 26, 2008. (Year: 2008).*
(Continued)

*Primary Examiner* — Khoi H Tran
*Assistant Examiner* — Jorge O Peche

(57) ABSTRACT

A method and system for controlling at least one robotically controlled surgical tool via vocal activation include detecting a vocal command generated by a surgeon, converting said at least one surgeon in said surgical setting via said voice sensor. The vocal command is converted to operative instructions associated with a robotically controlled surgical tool to generate instructions according to a predetermined set of rules including at least one of a no fly zone rule and collision prevention rule.

12 Claims, 26 Drawing Sheets

Related U.S. Application Data continuation of application No. 15/481,496, filed on Apr. 7, 2017, now Pat. No. 10,866,783, which is a continuation-in-part of application No. 15/393,286, filed on Dec. 29, 2016, now Pat. No. 10,299,773, and a continuation-in-part of application No. 15/289,324, filed on Oct. 10, 2016, now Pat. No. 10,201,392, and a continuation-in-part of application No. 15/169,990, filed on Jun. 1, 2016, now Pat. No. 10,064,691, and a continuation-in-part of application No. 14/817,245, filed on Aug. 4, 2015, now Pat. No. 10,052,157, and a continuation-in-part of application No. 14/816,127, filed on Aug. 3, 2015, now Pat. No. 10,039,609, and a continuation-in-part of application No. 14/816,099, filed on Aug. 3, 2015, now Pat. No. 10,028,792, and a continuation-in-part of application No. 14/813,170, filed on Jul. 30, 2015, now Pat. No. 9,937,013, said application No. 15/393,286 is a continuation-in-part of application No. 14/813,170, filed on Jul. 30, 2015, now Pat. No. 9,937,013, said application No. 15/481, 496 is a continuation-in-part of application No. 14/753,902, filed on Jun. 29, 2015, now Pat. No. 9,757,206, and a continuation-in-part of application No. 14/752,949, filed on Jun. 28, 2015, now Pat. No. 9,757,204, said application No. 15/289,324 is a continuation of application No. 14/752,947, filed on Jun. 28, 2015, now Pat. No. 9,504,456, said application No. 15/169,990 is a continuation of application No. 14/752,947, filed on Jun. 28, 2015, now Pat. No. 9,504,456, said application No. 15/481,496 is a continuation-in-part of application No. 14/239,897, filed on Feb. 20, 2014, now Pat. No. 10,092,164, said application No. 14/816,099 is a continuation of application No. 14/150,939, filed on Jan. 9, 2014, now Pat. No. 9,204,939, said application No. 14/813,170 is a continuation of application No. 14/150,939, filed on Jan. 9, 2014, now Pat. No. 9,204,939, said application No. 14/752,949 is a division of application No. 14/150,939, filed on Jan. 9, 2014, now Pat. No. 9,204,939, said application No. 14/817,245 is a continuation-in-part of application No. 14/150,939, filed on Jan. 9, 2014, now Pat. No. 9,204,939, said application No. 14/752,947 is a division of application No. 14/150,939, filed on Jan. 9, 2014, now Pat. No. 9,204,939, said application No. 14/753,902 is a continuation-in-part of application No. 14/150,939, filed on Jan. 9, 2014, now Pat. No. 9,204,939, said application No. 14/816,127 is a continuation of application No. 14/150,939, filed on Jan. 9, 2014, now Pat. No. 9,204,939, which is a continuation-in-part of application No. PCT/IL2012/000310, filed as application No. PCT/IL2012/000309 on Aug. 21, 2012.

(60) Provisional application No. 62/319,289, filed on Apr. 7, 2016, provisional application No. 61/750,856, filed on Jan. 10, 2013, provisional application No. 61/525,779, filed on Aug. 21, 2011, provisional application No. 61/525,787, filed on Aug. 21, 2011, provisional application No. 61/525,789, filed on Aug. 21, 2011.

(51) Int. Cl.
  *G10L 15/22* (2006.01)
  *G10L 15/28* (2013.01)
  *A41D 13/11* (2006.01)
  *A61B 17/00* (2006.01)
  *A61B 34/20* (2016.01)

(52) U.S. Cl.
  CPC .... G10L 15/28 (2013.01); *A61B 2017/00017* (2013.01); *A61B 2017/00119* (2013.01); *A61B 2017/00132* (2013.01); *A61B 2017/00203* (2013.01); *A61B 2017/00221* (2013.01); *A61B 2017/00225* (2013.01); *A61B 2034/2048* (2016.02); *A61B 2034/2065* (2016.02)

(56) References Cited

U.S. PATENT DOCUMENTS

| | | | | |
|---|---|---|---|---|
| 4,955,891 A * | 9/1990 | Carol | ...................... | A61B 90/11 403/91 |
| 4,989,253 A * | 1/1991 | Liang | ................. | G02B 21/0012 704/E15.045 |
| 5,086,401 A * | 2/1992 | Glassman | ................. | A61F 2/46 606/88 |
| 5,154,723 A * | 10/1992 | Kubota | ................... | A61B 90/11 600/102 |
| 5,201,742 A * | 4/1993 | Hasson | ................... | A61B 90/11 606/1 |
| 5,211,165 A * | 5/1993 | Dumoulin | ................ | A61B 5/06 378/62 |
| 5,269,305 A * | 12/1993 | Corol | ...................... | A61B 90/11 378/20 |
| 5,313,306 A * | 5/1994 | Kuban | ................... | G06T 3/0018 348/240.99 |
| 5,372,147 A * | 12/1994 | Lathrop, Jr. | ........... | A61B 34/30 600/230 |
| 5,446,445 A * | 8/1995 | Bloomfield | ............ | B60L 50/51 340/539.22 |
| 5,494,034 A * | 2/1996 | Schlondorff | ........... | A61B 6/032 901/41 |
| 5,553,198 A * | 9/1996 | Wang | ..................... | A61B 34/70 901/1 |
| 5,571,072 A * | 11/1996 | Kronner | ............. | F16M 11/2035 600/102 |
| 5,572,999 A * | 11/1996 | Funda | .................. | B25J 17/0275 600/459 |
| 5,673,082 A * | 9/1997 | Wells | ................... | H04N 23/661 348/E13.005 |
| 5,684,531 A * | 11/1997 | Li | ........................... | G01C 3/085 382/153 |
| 5,774,841 A * | 6/1998 | Salazar | ................... | G10L 15/22 704/E15.04 |
| 5,820,623 A * | 10/1998 | Ng | ......................... | A61B 34/70 606/1 |
| 5,836,869 A * | 11/1998 | Kudo | ................. | A61B 1/00009 600/173 |
| 5,876,325 A * | 3/1999 | Mizuno | .................. | A61B 34/37 600/117 |
| 5,878,193 A * | 3/1999 | Wang | ..................... | A61B 34/70 600/117 |
| 5,905,773 A * | 5/1999 | Wong | ..................... | H04M 1/271 704/E15.044 |
| 5,911,036 A * | 6/1999 | Wright | ................... | A61B 90/36 345/157 |
| 5,960,363 A * | 9/1999 | Mizikovsky | .......... | H04M 1/724 379/444 |
| 5,971,976 A * | 10/1999 | Wang | ..................... | A61B 34/77 600/595 |
| 6,024,695 A * | 2/2000 | Taylor | .................. | B25J 17/0275 600/102 |
| 6,100,501 A * | 8/2000 | von der Heyde | ...... | A61B 17/50 362/120 |
| 6,102,850 A * | 8/2000 | Wang | ..................... | A61B 34/37 600/102 |
| 6,106,511 A * | 8/2000 | Jensen | .................. | A61B 34/70 606/1 |
| 6,179,776 B1* | 1/2001 | Adams | ............... | A61B 1/00078 600/146 |

(56) References Cited

U.S. PATENT DOCUMENTS

| | | | | |
|---|---|---|---|---|
| 6,192,267 B1* | 2/2001 | Scherninski | A61B 5/0071 | 600/431 |
| 6,368,332 B1* | 4/2002 | Salcudean | A61B 90/50 | 606/1 |
| 6,387,044 B1* | 5/2002 | Tachibana | A61B 1/00135 | 600/114 |
| 6,405,029 B1* | 6/2002 | Nilsson | H04W 4/24 | 455/406 |
| 6,451,027 B1* | 9/2002 | Cooper | A61B 1/00149 | 901/19 |
| 6,463,361 B1* | 10/2002 | Wang | A61B 34/70 | 704/E15.045 |
| 6,632,170 B1* | 10/2003 | Bohanan | A61B 90/50 | 600/102 |
| 6,723,106 B1* | 4/2004 | Charles | B25J 9/1065 | 606/130 |
| 6,786,896 B1* | 9/2004 | Madhani | A61B 34/30 | 606/1 |
| 6,811,608 B1* | 11/2004 | Stewart | C30B 7/00 | 117/69 |
| 6,850,794 B2* | 2/2005 | Shahidi | A61B 90/36 | 600/427 |
| 6,946,812 B1* | 9/2005 | Martin | B25J 9/1689 | 318/568.22 |
| 6,947,893 B1* | 9/2005 | Iwaki | G10L 19/018 | 704/E19.009 |
| 7,048,745 B2* | 5/2006 | Tierney | G16H 40/63 | 606/1 |
| 7,087,049 B2* | 8/2006 | Nowlin | A61B 34/35 | 606/1 |
| 7,313,430 B2* | 12/2007 | Urquhart | A61B 90/14 | 600/428 |
| 7,319,897 B2* | 1/2008 | Leitner | A61B 17/1714 | 600/463 |
| 7,674,270 B2* | 3/2010 | Layer | A61B 17/3403 | 600/587 |
| 7,833,152 B2* | 11/2010 | Chatenever | A61B 1/00045 | 600/173 |
| 8,079,950 B2* | 12/2011 | Stern | A61B 34/70 | 600/109 |
| 9,302,393 B1* | 4/2016 | Rosen | G06N 3/008 | |
| 10,292,777 B1* | 5/2019 | Adelman | A61B 34/25 | |
| 10,603,127 B2* | 3/2020 | Hasser | G16H 40/67 | |
| 11,561,762 B2* | 1/2023 | Atarot | G06F 3/167 | |
| 2002/0026096 A1* | 2/2002 | Motoki | A61B 1/00042 | 600/117 |
| 2002/0082612 A1* | 6/2002 | Moll | G16H 40/63 | 606/130 |
| 2002/0091301 A1* | 7/2002 | Levin | A61B 17/00234 | 600/37 |
| 2002/0097332 A1* | 7/2002 | Martin | G08B 13/19689 | 348/E7.087 |
| 2002/0133174 A1* | 9/2002 | Charles | A61B 34/37 | 606/130 |
| 2002/0151795 A1* | 10/2002 | Palti | A61B 8/06 | 600/455 |
| 2002/0166403 A1* | 11/2002 | Choset | B25J 17/0275 | 74/423 |
| 2002/0167422 A1* | 11/2002 | Andre | G06F 3/0338 | 341/34 |
| 2003/0055410 A1* | 3/2003 | Evans | A61B 34/32 | 606/1 |
| 2003/0062858 A1* | 4/2003 | Shimizu | B25J 9/1615 | 318/34 |
| 2003/0135203 A1* | 7/2003 | Wang | A61B 34/30 | 606/1 |
| 2003/0144649 A1* | 7/2003 | Ghodoussi | A61B 34/75 | 606/1 |
| 2003/0182122 A1* | 9/2003 | Horinaka | G06N 3/008 | 704/E15.04 |
| 2003/0216833 A1* | 11/2003 | Mukai | B25J 9/1602 | 700/245 |
| 2003/0233102 A1* | 12/2003 | Nakamura | A61B 34/30 | 606/130 |
| 2003/0235183 A1* | 12/2003 | Skelton | H04M 3/562 | 370/352 |
| 2004/0015053 A1* | 1/2004 | Bieger | A61B 5/06 | 600/102 |
| 2004/0024387 A1* | 2/2004 | Payandeh | A61B 90/11 | 606/1 |
| 2004/0089777 A1* | 5/2004 | Schilt | A61B 90/50 | 248/292.12 |
| 2004/0111183 A1* | 6/2004 | Sutherland | A61B 34/76 | 700/245 |
| 2004/0138524 A1* | 7/2004 | Ueda | A61B 90/50 | 600/102 |
| 2004/0204627 A1* | 10/2004 | Furukawa | A61B 1/00055 | 600/118 |
| 2004/0225185 A1* | 11/2004 | Obata | A61B 1/042 | 600/118 |
| 2004/0239631 A1* | 12/2004 | Gresham | G06F 3/0216 | 345/168 |
| 2004/0243147 A1* | 12/2004 | Lipow | A61B 34/74 | 606/130 |
| 2004/0260538 A1* | 12/2004 | Morse | G10L 15/26 | 704/E15.045 |
| 2005/0119527 A1* | 6/2005 | Banik | A61B 1/00066 | 600/117 |
| 2005/0123189 A1* | 6/2005 | Bayer | G01S 15/8993 | 382/128 |
| 2005/0162383 A1* | 7/2005 | Rosenberg | G06F 3/03545 | 345/156 |
| 2005/0171557 A1* | 8/2005 | Shoham | A61B 34/30 | 606/130 |
| 2005/0177276 A1* | 8/2005 | Morel | B25J 9/1671 | 700/245 |
| 2005/0272971 A1* | 12/2005 | Ohnishi | A61B 1/00009 | 600/101 |
| 2006/0100501 A1* | 5/2006 | Berkelman | A61B 17/3403 | 600/415 |
| 2006/0149824 A1* | 7/2006 | Park | H04L 67/125 | 709/206 |
| 2006/0161303 A1* | 7/2006 | Wang | A61B 34/37 | 700/259 |
| 2006/0167440 A1* | 7/2006 | Cooper | A61B 34/71 | 606/1 |
| 2006/0178777 A1* | 8/2006 | Park | H04L 12/2818 | 704/275 |
| 2007/0021713 A1* | 1/2007 | Kumar | A61M 3/0258 | 604/27 |
| 2007/0078303 A1* | 4/2007 | Abe | G16H 50/20 | 600/101 |
| 2007/0083480 A1* | 4/2007 | Ozaki | G16H 40/60 | 706/924 |
| 2007/0112463 A1* | 5/2007 | Roh | B25J 9/1656 | 700/245 |
| 2008/0071140 A1* | 3/2008 | Gattani | A61B 34/20 | 600/117 |
| 2008/0077158 A1* | 3/2008 | Haider | G16H 40/63 | 606/130 |
| 2009/0018419 A1* | 1/2009 | Torch | G06F 3/013 | 348/78 |
| 2009/0036902 A1* | 2/2009 | DiMaio | A61B 8/12 | 606/130 |
| 2009/0216534 A1* | 8/2009 | Somasundaram | G16H 40/20 | 705/28 |
| 2009/0234639 A1* | 9/2009 | Teague | G06N 5/02 | 704/E15.04 |
| 2009/0240259 A1* | 9/2009 | Nelson | A61B 34/76 | 606/130 |
| 2009/0299751 A1* | 12/2009 | Jung | G10L 15/26 | 901/50 |
| 2010/0076600 A1* | 3/2010 | Cross | H04W 4/70 | 700/264 |
| 2010/0274087 A1* | 10/2010 | Diolaiti | A61B 34/30 | 700/275 |
| 2010/0298976 A1* | 11/2010 | Sugihara | A63H 11/20 | 700/258 |

(56) References Cited

U.S. PATENT DOCUMENTS

| | | | |
|---|---|---|---|
| 2010/0308999 A1* | 12/2010 | Chornenky | G08B 6/00 700/245 |
| 2011/0118748 A1* | 5/2011 | Itkowitz | A61B 90/98 606/130 |
| 2011/0118870 A1* | 5/2011 | Sugihara | G06N 3/008 700/245 |
| 2011/0175989 A1* | 7/2011 | Islam | A61B 1/0004 348/61 |
| 2012/0022696 A1* | 1/2012 | Aoussat | A61B 34/70 700/275 |
| 2012/0158019 A1* | 6/2012 | Tenney | A61B 34/10 606/133 |
| 2012/0197182 A1* | 8/2012 | Millman | A61B 34/74 604/95.01 |
| 2013/0123804 A1* | 5/2013 | Sholev | A61B 34/70 340/12.5 |
| 2013/0190776 A1* | 7/2013 | Zhang | A61B 17/3468 606/133 |
| 2013/0218339 A1* | 8/2013 | Maisonnier | B25J 13/003 700/257 |
| 2013/0325450 A1* | 12/2013 | Levien | G10L 15/07 704/201 |
| 2013/0325451 A1* | 12/2013 | Levien | G10L 15/07 704/201 |
| 2014/0005489 A1* | 1/2014 | Charles | A61B 17/0206 600/235 |
| 2014/0116469 A1* | 5/2014 | Kim | A47L 11/4061 15/319 |
| 2014/0119737 A1* | 5/2014 | Bakish | A41D 13/11 398/133 |
| 2014/0194896 A1* | 7/2014 | Frimer | A61B 1/00149 606/130 |
| 2014/0221738 A1* | 8/2014 | Sholev | A61B 90/50 600/149 |
| 2014/0222023 A1* | 8/2014 | Kim | A61B 34/30 606/130 |
| 2014/0378763 A1* | 12/2014 | Atarot | A61B 90/37 600/109 |
| 2015/0031953 A1* | 1/2015 | Atarot | A61B 1/00042 600/118 |
| 2016/0103810 A1* | 4/2016 | Hanning | G16H 30/40 715/226 |
| 2016/0228204 A1* | 8/2016 | Quaid | A61B 34/10 |
| 2016/0246929 A1* | 8/2016 | Zenati | G10L 15/22 |
| 2016/0283191 A1* | 9/2016 | Lu | G06F 3/165 |
| 2016/0314716 A1* | 10/2016 | Grubbs | G09B 23/306 |
| 2016/0314717 A1* | 10/2016 | Grubbs | G09B 23/32 |
| 2016/0343372 A1* | 11/2016 | Motomura | G06F 16/00 |
| 2016/0361125 A1* | 12/2016 | Balicki | A61B 34/30 |
| 2017/0047066 A1* | 2/2017 | Liu | G10L 15/30 |
| 2017/0125008 A1* | 5/2017 | Maisonnier | G10L 15/22 |
| 2017/0156674 A1* | 6/2017 | Hochman | A61B 5/389 |
| 2017/0156808 A1* | 6/2017 | Auld | A61B 34/70 |
| 2017/0206064 A1* | 7/2017 | Breazeal | B25J 11/0005 |
| 2017/0212723 A1* | 7/2017 | Atarot | G06F 3/167 |
| 2017/0326724 A1* | 11/2017 | Wei | B25J 5/007 |
| 2017/0330413 A1* | 11/2017 | Sato | G07F 17/34 |
| 2017/0361468 A1* | 12/2017 | Cheuvront | A47L 9/2857 |
| 2018/0000173 A1* | 1/2018 | Tsaur | G10K 11/24 |
| 2018/0025248 A1* | 1/2018 | Shan | G06F 3/167 382/189 |
| 2018/0042680 A1* | 2/2018 | DiMaio | G16H 20/40 |
| 2018/0092706 A1* | 4/2018 | Anderson | A61B 34/74 |
| 2018/0182375 A1* | 6/2018 | Fomin | G06V 20/41 |
| 2018/0199949 A1* | 7/2018 | Chien | A61B 17/1626 |
| 2018/0221240 A1* | 8/2018 | Yu | A61H 3/061 |
| 2018/0250086 A1* | 9/2018 | Grubbs | A61B 34/35 |
| 2018/0308478 A1* | 10/2018 | Ikeno | G10L 15/22 |
| 2018/0317725 A1* | 11/2018 | Lee | A47L 11/201 |
| 2018/0338806 A1* | 11/2018 | Grubbs | A61B 34/30 |
| 2019/0000578 A1* | 1/2019 | Yu | G06T 19/006 |
| 2019/0005848 A1* | 1/2019 | Garcia Kilroy | G06T 3/20 |
| 2019/0107833 A1* | 4/2019 | Song | G06F 3/167 |
| 2019/0126488 A1* | 5/2019 | Sumiyoshi | G10L 15/22 |
| 2019/0290374 A1* | 9/2019 | Ramadorai | A61B 34/30 |
| 2019/0355354 A1* | 11/2019 | Geng | G10L 15/22 |
| 2019/0361664 A1* | 11/2019 | Xiong | G10L 15/22 |
| 2020/0133239 A1* | 4/2020 | Yamamoto | G06F 3/0484 |
| 2020/0160989 A1* | 5/2020 | Korehisa | A61B 1/307 |
| 2020/0382695 A1* | 12/2020 | Song | H04N 23/695 |
| 2020/0411015 A1* | 12/2020 | Kim | G10L 15/16 |
| 2021/0005205 A1* | 1/2021 | Choi | G10L 15/26 |
| 2021/0016431 A1* | 1/2021 | Kim | G10L 15/22 |
| 2021/0170606 A1* | 6/2021 | Shin | G06F 3/04886 |
| 2021/0333776 A1* | 10/2021 | Sato | G05B 19/4155 |
| 2021/0354300 A1* | 11/2021 | Nagao | B25J 13/003 |
| 2023/0123443 A1* | 4/2023 | Atarot | G06F 3/167 704/275 |

FOREIGN PATENT DOCUMENTS

| | | | | |
|---|---|---|---|---|
| EP | 2754383 A2 * | 7/2014 | | A61B 1/00006 |
| KR | 20120111510 A * | 10/2012 | | |
| KR | 20130060952 A * | 6/2013 | | |
| KR | 20140126322 A * | 10/2014 | | |
| KR | 102102810 B1 * | 4/2020 | | |
| KR | 102216839 B1 * | 2/2021 | | |
| WO | WO-2008127316 A1 * | 10/2008 | | G06F 3/012 |
| WO | WO-2017175232 A1 * | 10/2017 | | A41D 13/11 |
| WO | WO-2022080788 A1 * | 4/2022 | | |
| WO | WO-2023162248 A1 * | 8/2023 | | |

OTHER PUBLICATIONS

"Human-computer interfaces for interaction with surgical tools in robotic surgery;" Staub et al., 2012 4th IEEE RAS & EMBS International Conference on Biomedical Robotics and Biomechatronics (BioRob) (pp. 81-86); Jun. 1, 2012. (Year: 2012).*

"A Study on Speech Recognition Control for a Surgical Robot;" Zinchenko et al., IEEE Transactions on Industrial Informatics (vol. 13, Issue: 2, pp. 607-615); Apr. 1, 2017. (Year: 2017).*

* cited by examiner

VOCALLY ACTUATED SURGICAL CONTROL SYSTEM

CROSS REFERENCE TO RELATED APPLICATIONS

This application is a continuation of U.S. application Ser. No. 17/064,549, filed Oct. 6, 2020, which is a continuation of U.S. application Ser. No. 15/481,496, filed Apr. 7, 2017, now U.S. Pat. No. 10,866,783, which claims priority from U.S. Provisional Application No. 62/319,289, filed Apr. 7, 2016, and which is a Continuation-In-Part Application of the following applications hereby incorporated by reference in their entirety:

- U.S. application Ser. No. 14/239,897, filed Feb. 20, 2014, which is a National Stage Entry of PCT International Application No. PCT/IL2012/000309, filed Aug. 21, 2012, claiming priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/752,949, filed Jun. 28, 2015, which is a Division of U.S. application Ser. No. 14/150,939, filed Jan. 9, 2014 (U.S. Pat. No. 9,204,939, issued Dec. 8, 2015), claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/753,902, filed Jun. 29, 2015, which is a Continuation-In-Part of U.S. application Ser. No. 14/150,939, filed Jan. 9, 2014 (U.S. Pat. No. 9,204,939, issued Dec. 8, 2015), claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/813,170, filed Jul. 30, 2015, which is Continuation of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/816,127, filed Aug. 3, 2015, which is a Continuation-In-Part of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/816,099, filed Aug. 3, 2015, which is a Continuation of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 14/817,245, filed Aug. 4, 2015, which is a Continuation-In-Part of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 15/169,990, filed Jun. 1, 2016, which is a Continuation of U.S. application Ser. No. 14/752,947, filed Jun. 28, 2015 (U.S. Pat. No. 9,504,456, issued Nov. 29, 2016), which is a Division of U.S. application Ser. No. 14/150,939, filed Jan. 9, 2014 (U.S. Pat. No. 9,204,939, issued Dec. 8, 2015), claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 15/289,324, filed Oct. 10, 2016, which is a Continuation of U.S. application Ser. No. 14/752,947, filed Jun. 28, 2015 (U.S. Pat. No. 9,504,456, issued Nov. 29, 2016), which is a Division of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.
- U.S. application Ser. No. 15/393,286, filed Dec. 29, 2016, which is a Continuation-In-Part of U.S. application Ser. No. 14/813,170, filed Jul. 30, 2015, which is a Continuation of U.S. application Ser. No. 14/150,939, filed Jan. 9, 2014 (U.S. Pat. No. 9,204,939, issued Dec. 8, 2015) claiming priority from U.S. Provisional Application No. 61/750,856, filed Jan. 10, 2013, and being a Continuation-In-Part of PCT International Application No. PCT/IL2012/000310, filed Aug. 21, 2012, which claims priority from U.S. Provisional Application No. 61/525,789, filed Aug. 21, 2011, U.S. Provisional Application No. 61/525,779, filed Aug. 21, 2011, and U.S. Provisional Application No. 61/525,787, filed Aug. 21, 2011.

FIELD OF THE INVENTION

The present invention generally relates to the field of control systems. More particularly, the present invention relates to a vocally activated system that controls a plurality of apparatus in a surgical setting.

BACKGROUND OF THE INVENTION

During many operating procedures, more than one surgical assistant is required to adjust various apparatus such as lighting, operating table, microscope, and endoscope so that the surgeon/operating staff can continue his or her work without stop to change setting of required apparatus. The need for two or more operators to work two separate systems as one seamless unit is a major challenge in surgery. Additionally, extra personnel add cost to the procedure and place a burden on operating room resources such as floor space and room ventilation and cooling apparatus.

Recent advancement in speech recognition leads to development of various voice activated or assisted control applications. Examples of these applications include assistance in generation and manipulation of medical images, adjustment of position of operating tables and manipulation of surgical devices such as microscopes.

U.S. Pat. No. 6,591,239 disclosed a voice controlled surgical suite for controlling a plurality of devices including a surgical table, a surgical lighthead, surgical camera and task light devices by a single human.

U.S. Pat. No. 6,747,566 disclosed a voice-activated remote control unit which is configured for use with one or more electrical apparatuses, such as a TV set, a DVD player, a stereo system, an air conditioner, for the purpose of allowing the user to remotely turn on/off and control the operations of these electrical apparatuses through voice-activation.

U.S. Pat. No. 7,286,992 disclosed a voice control system for surgical microscopes, which has a voice operating unit and at least one other operating unit such as a manual operating unit, a foot-controlled operating unit, and/or an eye-controlled operating unit. The control apparatus executes one set of microscope functions via the voice operating unit and another set of microscope functions via the non-voice operating units.

U.S. Pat. No. 6,785,358 disclosed a voice activated diagnostic imaging control user interface. This invention provided a voice activated control system for a medical imaging system. The control subsystem comprises an audio microphone configured to be positioned for receiving audio input from an operator, an audio amplifier for receiving audio signals generated by the microphone, and an audio signal processor coupled to the amplifier for processing amplified audio signals from the amplifier. The processing comprising word recognition.

However, in these disclosed systems, voices are picked up via voice sensors that are not immediately attached to the surgeon/operating staff or not in a constant position related to the surgeon, which can potentially lead to low signal and significant background noise resulting in more errors in the speech recognition process. Therefore, there is a still unmet need to develop a sensitive and accurate vocally activated control system and method thereof for controlling a plurality of apparatus in the operating room.

SUMMARY OF THE INVENTION

It is another object of the present invention to provide a vocally activated control system for controlling at least one apparatus in a surgical setting, said vocally activated control system comprises:
  a. a voice sensor configured to detect at least one vocal command generated by at least one surgeon in said surgical setting;
  b. a signal transmitter operatively connected to said voice sensor, said transmitter is configured to convert said at least one vocal command into at least one transmittable vocal signal and transmit said at least one transmittable vocal signal;
  c. a processor operatively connected to said signal transmitter configured to receive said at least one transmittable vocal signal, said processor is configured to convert said at least one transmittable vocal signal to at least one predetermined set of operative instructions associated with said at least one apparatus, said at least one predetermined set of operative instructions comprising at least one instruction; and
  d. at least one control means operatively connected to said processor and said at least one apparatus; said at least one control means is configured to receive said predetermined set of operative instructions and to cause said at least one apparatus to operate accordingly;
  wherein said voice sensor and said transmitter are integrated within a wearable element.

It is another object of the present invention to provide the vocally activated control system as defined above, wherein a location of said wearable element is selected from a group consisting of: integrated within a surgical wearable element wearable by said at least one surgeon, integrated within said system, attachable to at least a portion of said system, and any combination thereof.

It is another object of the present invention to provide the vocally activated control system as defined above, wherein surgical wearable element is selected from a group consisting of a mask, a helmet, a headpiece, a cap, a shoe cover, a glove, a hospital robe, surgical garb, a gown, a neckpiece, a wristlet, an armlet, an earpiece and any combination thereof.

It is another object of the present invention to provide the vocally activated control system as defined above, wherein at least one of the following is held true:
  a. said at least one apparatus is selected from a group consisting of endoscope, microscope, robotic arm, laparoscopy, operating light, surgical table, surgical camera, imaging device, injection device, measurement device, optical device, stereotactic device, positioning device, suction device, sealing device, ablation means, resection means, dissection means and any combination thereof;
  b. said voice sensor comprises:
    a microphone configured to pick up said at least one vocal command; and
    a voice recognition unit configured to perform a vocal recognition algorithm on said at least one vocal command picked up by said microphone thereby to recognize said at least one vocal command; said vocal recognition algorithm is selected from a group consisting of hidden markov model, dynamic time warping, neural networks, deep neural networks and any combination thereof;

c. said processor further comprises a storage unit for storing a database of digital vocal signals;
d. said signal transmitter is selected from a group consisting of RFID, IR emitter, digital RF, RF Communication, Bluetooth device and any combination thereof;
e. said at least one vocal command is selected from a group consisting of "on", "off", "zoom in", "zoom out", "left", "right", "up", "down", "start", "stop", "increase", "decrease", "open", "close", "suture", "incise", "ablate", "select" and any combination thereof;
f. said voice sensor is connected to said signal transmitter through wired or wireless means;
g. said processor is connected to said signal transmitter through wired or wireless means;
h. said system further comprises a feedback mechanism configured to receive a member of a group consisting of an audio signal, a visual signal and any combination thereof and to indicate status of execution of said vocal command; and
i. at least one response to at least one said at least one vocal command is selected from a group consisting of a smart response, a dumb response and any combination thereof, said smart response being configured to take into account at least one feature of the surrounding environment and said dumb response not taking into account any feature of said surrounding environment; said feature selected from a group consisting of a hazard or obstacle, an interference between two surgical tools, an interference between two parts of an apparatus, interference between two apparatus, possibility of damage to a portion of a patient, and any combination thereof.

It is another object of the present invention to provide the vocally activated control system as defined above, wherein said at least one vocal command comprises at least one complex sentence; said voice sensor further comprising a context recognition unit configured to recognize said at least one vocal command from said complex sentence.

It is another object of the present invention to provide the vocally activated control system as defined above, wherein said vocal command can be unqualified or can comprise at least one qualifier, said at least one qualifier configured to modify at least one component of a response, at least one of the following is being held true:
a. wherein said qualifier is selected from a group consisting of an amount, a surgical tool, an apparatus, and any combination thereof; and
b. wherein said amount is either a fixed-term value or a fractional value.

It is another object of the present invention to provide the vocally activated control system as defined above, wherein said unqualified command is configured to comprise a predetermined qualifier or to continue a process until stopped.

It is another object of the present invention to provide the vocally activated control system as defined above, wherein at least one of the following is held true:
a. said predetermined qualifier is an amount, said amount being either a fixed-term value or a fractional value;
b. said vocal command is configured to reversibly select a member of a group consisting of an apparatus, a surgical tool, at least a portion of a patient, and any combination thereof; a duration of said selection is selected from a group consisting of: for a predetermined time, or until reception of a change command;
c. said vocal command is configured to change a member of a group consisting of: a predetermined amount; a value, a type of value and any combination thereof.

It is another object of the present invention to provide the vocally activated control system as defined above, wherein said conversion of said transmittable vocal signal to said at least one predetermined set of operative instructions is via a predetermined set of rules, said at least one predetermined set of rules comprising at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, go-to rule, change of speed rule and any combination thereof; said allowed movement being permitted by said controller and said restricted movement being denied by said controller according to said predetermined set of rules.

It is another object of the present invention to provide the vocally activated control system as defined above, wherein at least one of the following is held true:
a. at least one said apparatus comprises a maneuvering subsystem configured to spatially reposition said at least one surgical tool according to said predetermined set of rules;
b. said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement is a movement in which said at least one surgical tool is located substantially in at least one of said n 3D spatial positions of said predefined route, and said restricted movement is a movement in which said location of said at least one surgical tool is substantially different from said n 3D spatial positions of said predefined route.
c. said environmental rule comprises a comprises a communicable database; said communicable database configured to receive at least one real-time image of said surgical environment and is configured to perform real-time image processing of the same and to determine the 3D spatial position of at least one hazard or obstacle in said surgical environment; said environmental rule is configured to determine said allowed movement an said restricted movement according to said hazards or obstacles in said surgical environment, such that said restricted movement is a movement in which said at least one surgical tool is located substantially in at least one of said 3D spatial positions, and said allowed movement is a movement in which the location of said at least one surgical tool is substantially different from said 3D spatial positions; said at least one hazard or obstacle being selected from a group consisting of tissue, a surgical tool, an organ, an endoscope and any combination thereof;
d. said proximity rule is configured to define at least one of a predetermined distance between at least two surgical tools and a predetermined angle between at least two surgical tools; for said predetermined distance, said allowed movement is a movement which is within the range or out of the range of said predetermined distance and said restricted movement is a movement which is out of the range or within the range of said predetermined distance; for said predetermined angle; said allowed movement is a movement which is within the range or out of the range of said predetermined angle and said restricted movement is a movement which is out of the range or within the range of said predetermined angle;

e. said collision prevention rule is configured to define a predetermined distance between said at least one surgical tool and an anatomical element within said surgical environment; said allowed movement is a movement which is in a range that is larger than said predetermined distance, and said restricted movement is a movement which is in a range that is smaller than said predetermined distance; said anatomical element being selected from a group consisting of tissue, organ, another surgical tool and any combination thereof;

f. said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movement is a movement in which said at least one of said surgical tool is located substantially in at least one of said n 3D spatial positions, and said allowed movement is a movement in which the location of said at least one surgical tool is substantially different from said n 3D spatial positions;

g. said preferred volume zone rule comprises a communicable database comprising n 3D spatial positions; n is an integer greater than or equal to 2; said n 3D spatial positions provides said preferred volume zone; said preferred volume zone rule is configured to determine said allowed movement of said surgical tool within said n 3D spatial positions and restricted movement of said surgical tool outside said n 3D spatial positions, such that said allowed movement is a movement in which at least a portion of said surgical tool is located substantially in at least one of said n 3D spatial positions, and said restricted movement is a movement in which the location of said surgical tool is substantially different from said n 3D spatial positions;

h. said history-based rule comprises a communicable database storing each 3D spatial position of each of said surgical tool, such that each movement of each surgical tool is stored; said history-based rule is configured to determine said allowed movement and said restricted movement according to historical movements of said at least one surgical tool, such that said allowed movement is a movement in which said at least one surgical tool is located substantially in at least one of said 3D spatial positions, and said restricted movement is a movement in which the location of said at least one surgical tool is substantially different from said n 3D spatial positions; and i. said maneuvering subsystem is configured to spatially reposition said at least one surgical tool during a surgery according to said predetermined set of rules, such that if said movement of said at least one surgical tool is a restricted movement, said maneuvering subsystem prevents said movement;

It is another object of the present invention to provide the vocally activated control system as defined above, wherein said system is configured to provide an alert of said restricted movement of said at least one surgical tool.

It is another object of the present invention to provide the vocally activated control system as defined above, wherein said operator input rule comprises a communicable database; said communicable database is configured to receive an input from the operator of said system regarding said allowed movement and said restricted movement of said at least one surgical tool; at least one of the following being held true:

a. said input comprises n 3D spatial positions; n is an integer greater than or equal to 2; wherein at least one of which is defined as allowed location and at least one of which is defined as restricted location, such that said allowed movement is a movement in which said at least one surgical tool is located substantially in at least one of said n 3D spatial positions, and said restricted movement is a movement in which the location of said at least one surgical tool is substantially different from said n 3D spatial positions.

b. said input comprises at least one rule according to which said allowed movement and said restricted movement of said at least one surgical tool are determinable, such that the spatial position of said at least one surgical tool is controlled by said controller according to said allowed movement and said restricted movement; said predetermined set of rules comprising at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof; and c. said operator input rule converts an allowed movement to a restricted movement and a restricted movement to an allowed movement.

It is another object of the present invention to provide the vocally activated control system as defined above, wherein said allowed movement is permitted by said controller and said restricted movement is denied by said controller.

It is another object of the present invention to provide the vocally activated control system as defined above, wherein at least one of the following is being held true (a) said system additionally comprises an endoscope; said endoscope is configured to provide real-time image of said surgical environment; (b) at least one of said surgical tools is an endoscope configured to provide real-time image of said surgical environment.

It is another object of the present invention to provide the vocally activated control system as defined above, wherein at least one of the following is held true:

a. said most used tool rule comprises a communicable database counting the amount of movement of each of said surgical tools; said most used tool rule is configured to constantly position said endoscope to track the movement of the most moved surgical tool; said alert being selected from a group consisting of audio signaling, voice signaling, light signaling, flashing signaling and any combination thereof;

b. said right tool rule is configured to determine said allowed movement of said endoscope according to the movement of the surgical tool positioned to right of said endoscope; further wherein said left tool rule is configured to determine said allowed movement of said endoscope according to the movement of the surgical tool positioned to left of said endoscope;

c. said tagged tool rule comprises means configured to tag at least one surgical tool within said surgical environment and to determine said allowed movement of said endoscope to constantly track the movement of said tagged surgical tool;

d. said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, such that said allowed movement is a movement in which said endoscope is located substantially in at least one of said n 3D spatial positions, and said restricted movement is a movement in which the location of said endoscope is substantially different from said n 3D spatial positions;

e. said preferred tool rule comprises a communicable database, said database stores a preferred tool; said preferred tool rule is configured to determine said allowed movement of said endoscope to constantly track the movement of said preferred tool;

f. said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics; such that said allowed movement is a movement of said endoscope which tracks said at least one of said at least one surgical tool having said predetermined characteristics; said predetermined characteristics of said surgical tool being selected from a group consisting of: physical dimensions, structure, weight, sharpness, and any combination thereof; and g. said movement detection rule comprises a communicable database comprising the real-time 3D spatial positions of each of said surgical tool; said movement detection rule is configured to detect movement of said at least one surgical tool when a change in said 3D spatial positions is received, such that said allowed movement is a movement in which said endoscope is re-directed to focus on the moving surgical tool.

It is another object of the present invention to provide the vocally activated control system as defined above, additionally comprising at least one location estimator, wherein said at least one location estimator comprises at least one endoscope configured to acquire real-time images of said surgical environment within said human body; and at least one surgical instrument spatial location software configured to receive said real-time images of said surgical environment and to estimate said 3D spatial position of said at least one surgical tool.

It is another object of the present invention to provide the vocally activated control system as defined above, wherein at least one of the following is held true:

a. said at least one location estimator comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element;

b. said at least one location estimator is an interface subsystem between a surgeon and the at least one surgical tool, the interface subsystem comprises:
 i. at least one array comprising N regular or pattern light sources, where N is a positive integer;
 ii. at least one array comprising M cameras, each of the M cameras, where M is a positive integer;
 iii. optional optical markers and means for attaching the optical marker to the at least one surgical tool; and;
 iv. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to provide a method of controlling at least one apparatus in a surgical setting via vocal activation, said method comprises steps of:

a. providing a vocally activated control system comprising:
 i. a voice sensor configured to detect at least one vocal command generated by at least one surgeon in said surgical setting;
 ii. a signal transmitter operatively connected to said voice sensor, said transmitter is configured to convert said at least one vocal command into at least one transmittable vocal signal and transmit said at least one transmittable vocal signal;
 iii. a processor operatively connected to said signal transmitter configured to receive said at least one digital transmittable vocal signal, said processor is configured to convert said at least one transmittable vocal signal to at least one predetermined set of operative instructions associated with said at least one apparatus, said at least one predetermined set of operative instructions comprising at least one instruction; and,
 iv. at least one control means operatively connected to said processor and said at least one apparatus; said at least one control means is configured to receive said predetermined set of operative instructions and to cause said at least one apparatus to operate accordingly;

b. detecting said at least one vocal command generated by said at least one surgeon in said surgical setting via said voice sensor;

c. converting said at least one vocal command into a transmittable vocal signal via said signal transmitter;

d. transmitting said transmittable vocal signal using said signal transmitter;

e. receiving said transmittable vocal signal through said processor operatively connected to said transmitter;

f. converting said transmittable vocal signal to said at least one predetermined set of operative instructions associated with said at least one apparatus via said processor; and g. receiving said predetermined set of instructions by said at least one control means operatively connected to said processor and said at least one apparatus; thereby operating said at least one apparatus according to said predetermined set of instructions using said at least one control means;

wherein said voice sensor and said transmitter are integrated within a wearable element.

It is another object of the present invention to provide the method as defined above, wherein a location of said wearable element is selected from a group consisting of: integrated within a surgical wearable element wearable by said at least one surgeon, integrated within said system, attachable to at least a portion of said system, and any combination thereof.

It is another object of the present invention to provide the method as defined above, wherein surgical wearable element is selected from a group consisting of a mask, a helmet, a headpiece, a cap, a shoe cover, a glove, a hospital robe, surgical garb, a gown, a neckpiece, a wristlet, a armlet, an earpiece and any combination thereof.

It is another object of the present invention to provide the method as defined above, wherein at least one of the following is held true:
  a. said at least one apparatus is selected from a group consisting of endoscope, microscope, robotic arm, laparoscopy, operating light, surgical table, surgical camera, imaging device, injection device, measurement device, optical device, stereotactic device, positioning device, suction device, sealing device, ablation means, resection means, dissection means and any combination thereof;
  b. said voice sensor comprises:
     a microphone configured to pick up said at least one vocal command; and
     a voice recognition unit configured to perform a vocal recognition algorithm on said at least one vocal command picked up by said microphone thereby to recognize said at least one vocal command; said vocal recognition algorithm is selected from a group consisting of hidden markov model, dynamic time warping, neural networks, deep neural networks and any combination thereof;
  c. said processor further comprises a storage unit for storing a database of digital vocal signals;
  d. said signal transmitter is selected from a group consisting of RFID, IR emitter, digital RF, RF Communication, Bluetooth device and any combination thereof;
  e. said at least one vocal command is selected from a group consisting of "on", "off", "zoom in", "zoom out", "left", "right", "up", "down", "start", "stop", "increase", "decrease", "open", "close", "suture", "incise", "ablate", "select" and any combination thereof;
  f. said voice sensor is connected to said signal transmitter through wired or wireless means;
  g. said processor is connected to said signal transmitter through wired or wireless means;
  h. said system further comprises a feedback mechanism configured to receive a member of a group consisting of an audio signal, a visual signal and any combination thereof and to indicate status of execution of said vocal command; and
  i. at least one response to at least one said at least one vocal command is selected from a group consisting of a smart response, a dumb response and any combination thereof, said smart response being configured to take into account at least one feature of the surrounding environment and said dumb response not taking into account any feature of said surrounding environment; said feature selected from a group consisting of a hazard or obstacle, an interference between two surgical tools, an interference between two parts of an apparatus, interference between two apparatus, possibility of damage to a portion of a patient, and any combination thereof.

It is another object of the present invention to provide the method as defined above, wherein said at least one vocal command comprises at least one complex sentence; said voice sensor further comprising a context recognition unit configured to recognize said at least one vocal command from said complex sentence.

It is another object of the present invention to provide the method as defined above, wherein said vocal command can be unqualified or can comprise at least one qualifier, said at least one qualifier configured to modify at least one component of a response, at least one of the following is being held true:
  a. said qualifier is selected from a group consisting of an amount, a surgical tool, an apparatus, and any combination thereof; and
  b. wherein said amount is either a fixed-term value or a fractional value.

It is another object of the present invention to provide method as defined above, wherein said unqualified command is configured to comprise a predetermined qualifier or to continue a process until stopped.

It is another object of the present invention to provide method as defined above, wherein at least one of the following is held true:
  a. said predetermined qualifier is an amount, said amount being either a fixed-term value or a fractional value;
  b. said vocal command is configured to reversibly select a member of a group consisting of an apparatus, a surgical tool, at least a portion of a patient, and any combination thereof; a duration of said selection is selected from a group consisting of: for a predetermined time, or until reception of a change command;
  c. said vocal command is configured to change a member of a group consisting of: a predetermined amount; a value, a type of value and any combination thereof.

It is another object of the present invention to provide method as defined above, wherein said conversion of said transmittable vocal signal to said at least one predetermined set of operative instructions is via a predetermined set of rules, said at least one predetermined set of rules comprising at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, go-to rule, change of speed rule and any combination thereof; said allowed movement being permitted by said controller and said restricted movement being denied by said controller according to said predetermined set of rules.

It is another object of the present invention to provide method as defined above, wherein at least one of the following is held true:
  a. at least one said apparatus comprises a maneuvering subsystem configured to spatially reposition said at least one surgical tool according to said predetermined set of rules;
  b. said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement is a movement in which said at least one surgical tool is located substantially in at least one of said n 3D spatial positions of said predefined route, and said restricted movement is a movement in which said location of said at least one surgical tool is substantially different from said n 3D spatial positions of said predefined route.

c. said environmental rule comprises a comprises a communicable database; said communicable database configured to receive at least one real-time image of said surgical environment and is configured to perform real-time image processing of the same and to determine the 3D spatial position of at least one hazard or obstacle in said surgical environment; said environmental rule is configured to determine said allowed movement an said restricted movement according to said hazards or obstacles in said surgical environment, such that said restricted movement is a movement in which said at least one surgical tool is located substantially in at least one of said 3D spatial positions, and said allowed movement is a movement in which the location of said at least one surgical tool is substantially different from said 3D spatial positions; said at least one hazard or obstacle being selected from a group consisting of tissue, a surgical tool, an organ, an endoscope and any combination thereof;

d. said proximity rule is configured to define at least one of a predetermined distance between at least two surgical tools and a predetermined angle between at least two surgical tools; for said predetermined distance, said allowed movement is a movement which is within the range or out of the range of said predetermined distance and said restricted movement is a movement which is out of the range or within the range of said predetermined distance; for said predetermined angle; said allowed movement is a movement which is within the range or out of the range of said predetermined angle and said restricted movement is a movement which is out of the range or within the range of said predetermined angle;

e. said collision prevention rule is configured to define a predetermined distance between said at least one surgical tool and an anatomical element within said surgical environment; said allowed movement is a movement which is in a range that is larger than said predetermined distance, and said restricted movement is a movement which is in a range that is smaller than said predetermined distance; said anatomical element being selected from a group consisting of tissue, organ, another surgical tool and any combination thereof;

f. said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movement is a movement in which said at least one of said surgical tool is located substantially in at least one of said n 3D spatial positions, and said allowed movement is a movement in which the location of said at least one surgical tool is substantially different from said n 3D spatial positions;

g. said preferred volume zone rule comprises a communicable database comprising n 3D spatial positions; n is an integer greater than or equal to 2; said n 3D spatial positions provides said preferred volume zone; said preferred volume zone rule is configured to determine said allowed movement of said surgical tool within said n 3D spatial positions and restricted movement of said surgical tool outside said n 3D spatial positions, such that said allowed movement is a movement in which at least a portion of said surgical tool is located substantially in at least one of said n 3D spatial positions, and said restricted movement is a movement in which the location of said surgical tool is substantially different from said n 3D spatial positions;

h. said history-based rule comprises a communicable database storing each 3D spatial position of each of said surgical tool, such that each movement of each surgical tool is stored; said history-based rule is configured to determine said allowed movement and said restricted movement according to historical movements of said at least one surgical tool, such that said allowed movement is a movement in which said at least one surgical tool is located substantially in at least one of said 3D spatial positions, and said restricted movement is a movement in which the location of said at least one surgical tool is substantially different from said n 3D spatial positions; and i. said maneuvering subsystem is configured to spatially reposition said at least one surgical tool during a surgery according to said predetermined set of rules, such that if said movement of said at least one surgical tool is a restricted movement, said maneuvering subsystem prevents said movement;

It is another object of the present invention to provide method as defined above, wherein said system is configured to provide an alert of said restricted movement of said at least one surgical tool.

It is another object of the present invention to provide method as defined above, wherein said operator input rule comprises a communicable database; said communicable database is configured to receive an input from the operator of said system regarding said allowed movement and said restricted movement of said at least one surgical tool; at least one of the following being held true:

a. said input comprises n 3D spatial positions; n is an integer greater than or equal to 2; wherein at least one of which is defined as allowed location and at least one of which is defined as restricted location, such that said allowed movement is a movement in which said at least one surgical tool is located substantially in at least one of said n 3D spatial positions, and said restricted movement is a movement in which the location of said at least one surgical tool is substantially different from said n 3D spatial positions.

b. said input comprises at least one rule according to which said allowed movement and said restricted movement of said at least one surgical tool are determinable, such that the spatial position of said at least one surgical tool is controlled by said controller according to said allowed movement and said restricted movement; said predetermined set of rules comprising at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof; and c. said operator input rule converts an allowed movement to a restricted movement and a restricted movement to an allowed movement.

It is another object of the present invention to provide method as defined above, wherein said allowed movement is permitted by said controller and said restricted movement is denied by said controller.

It is another object of the present invention to provide method as defined above, wherein at least one of the following is being held true (a) said system additionally comprises an endoscope; said endoscope is configured to provide real-time image of said surgical environment; (b) at least one of said surgical tools is an endoscope configured to provide real-time image of said surgical environment.

It is another object of the present invention to provide method as defined above, wherein at least one of the following is held true:
a. said most used tool rule comprises a communicable database counting the amount of movement of each of said surgical tools; said most used tool rule is configured to constantly position said endoscope to track the movement of the most moved surgical tool; said alert being selected from a group consisting of audio signaling, voice signaling, light signaling, flashing signaling and any combination thereof;
b. said right tool rule is configured to determine said allowed movement of said endoscope according to the movement of the surgical tool positioned to right of said endoscope; further wherein said left tool rule is configured to determine said allowed movement of said endoscope according to the movement of the surgical tool positioned to left of said endoscope;
c. said tagged tool rule comprises means configured to tag at least one surgical tool within said surgical environment and to determine said allowed movement of said endoscope to constantly track the movement of said tagged surgical tool;
d. said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, such that said allowed movement is a movement in which said endoscope is located substantially in at least one of said n 3D spatial positions, and said restricted movement is a movement in which the location of said endoscope is substantially different from said n 3D spatial positions;
e. said preferred tool rule comprises a communicable database, said database stores a preferred tool; said preferred tool rule is configured to determine said allowed movement of said endoscope to constantly track the movement of said preferred tool;
f. said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics; such that said allowed movement is a movement of said endoscope which tracks said at least one of said at least one surgical tool having said predetermined characteristics; said predetermined characteristics of said surgical tool being selected from a group consisting of: physical dimensions, structure, weight, sharpness, and any combination thereof; and
g. said movement detection rule comprises a communicable database comprising the real-time 3D spatial positions of each of said surgical tool; said movement detection rule is configured to detect movement of said at least one surgical tool when a change in said 3D spatial positions is received, such that said allowed movement is a movement in which said endoscope is re-directed to focus on the moving surgical tool.

It is another object of the present invention to provide method as defined above, additionally comprising at least one location estimator, wherein said at least one location estimator comprises at least one endoscope configured to acquire real-time images of said surgical environment within said human body; and at least one surgical instrument spatial location software configured to receive said real-time images of said surgical environment and to estimate said 3D spatial position of said at least one surgical tool.

It is another object of the present invention to provide method as defined above, wherein at least one of the following is held true:
a. said at least one location estimator comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element;
b. said at least one location estimator is an interface subsystem between a surgeon and the at least one surgical tool, the interface subsystem comprises:
  i. at least one array comprising N regular or pattern light sources, where N is a positive integer;
  ii. at least one array comprising M cameras, each of the M cameras, where M is a positive integer;
  iii. optional optical markers and means for attaching the optical marker to the at least one surgical tool; and;
  iv. a computerized algorithm operable via the controller, the computerized algorithm configured to record images received by each camera of each of the M cameras and to calculate therefrom the position of each of the tools, and further configured to provide automatically the results of the calculation to the human operator of the interface.

BRIEF DESCRIPTION OF THE FIGURES

In the following detailed description of the preferred embodiments, reference is made to the accompanying drawings that form a part hereof, and in which are shown by way of illustration specific embodiments in which the invention can be practiced. It is understood that other embodiments can be utilized and structural changes can be made without departing from the scope of the present invention. The present invention can be practiced according to the claims without some or all of these specific details. For the purpose of clarity, technical material that is known in the technical fields related to the invention has not been described in detail so that the present invention is not unnecessarily obscured. In the accompanying drawing:

DETAILED DESCRIPTION OF THE PREFERRED EMBODIMENTS

Figure 1A:
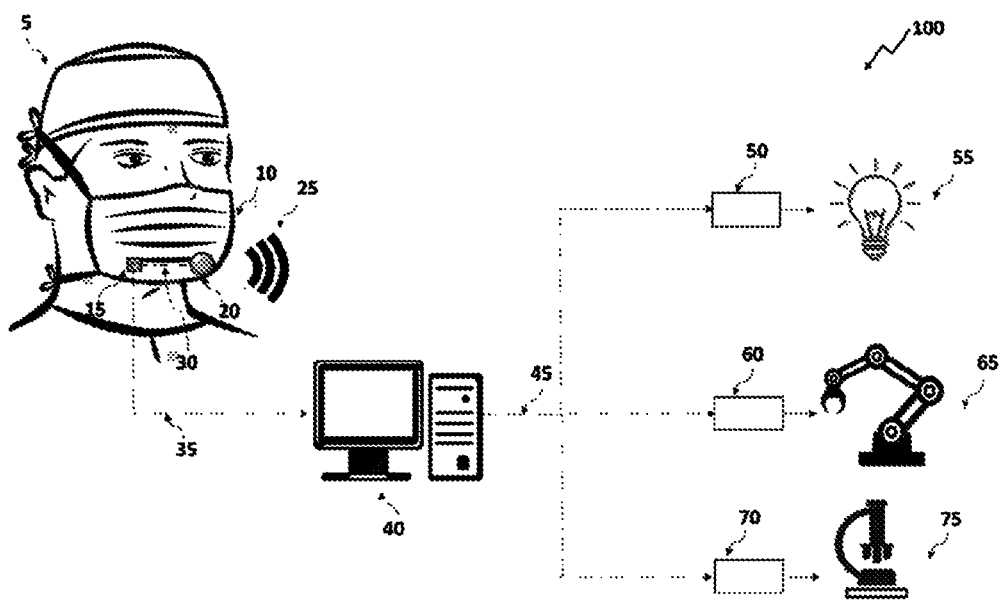
FIGS. 1a-1b is a schematic illustration of the vocally activated control system (100) according to a preferred embodiment of the present invention.

In the following detailed description of the preferred embodiments, reference is made to the accompanying drawings that form a part hereof, and in which are shown by way of illustration of specific embodiments in which the invention can be practiced. It is understood that other embodiments can be utilized and structural changes can be made without departing from the scope of the present invention. The present invention can be practiced according to the claims without some or all of these specific details. For the purpose of clarity, technical material that is known in the technical fields related to the invention has not been described in detail so that the present invention is not unnecessarily obscured. The essence of the present invention is to provide a vocally activated control system for controlling a plurality of apparatus in a surgical setting; the system includes a voice sensor and a signal transmitter integrated with a surgical mask worn by a surgeon/operating staff in the surgical setting.

The term "surgical setting" refers hereinafter to any environment where surgical procedures are performed. The most common example is an operating room. There could be one or more surgeons/operating staff involved in one surgical setting.

The term "surgical wearable element" refers hereinafter to any wearable element that can be worn by either a surgeon, nurse or any technician being in an operating room. Said element is selected from a group consisting of mask, helmet, headpiece, glove, hospital robe, surgical garb, gown and any combination thereof.

The term "surgeon" refers hereinafter to any professional person in the operating room. E.g., the operating surgeon or any of the operating staff (personnel).

The term "apparatus" refers hereinafter to any device or instrument in a surgical setting. The examples include but are not limited to endoscope, microscope, robotic arm, laparoscopy, operating light, surgical table, surgical camera, imaging device, injection device, measurement device, optical device, stereotactic device, positioning device, suction device, sealing device, ablation means, resection means, dissection means and any combination thereof.

The term "vocal" interchangeably refers hereinafter to "voice", anything relating to, or uttered with the voice, such as a vocal sound.

The term "vocal command" refers hereinafter to any verbal phrase that contains instructional information provided by a surgeon/operating staff to change at least one aspect of an apparatus. Examples include, but are not limited, to simple command including "on", "off", "zoom in", "zoom out", "left", "right", "up", "down", "start", "stop", "increase", "decrease", "open", "close", etc. More complex command include, but are not limited to "suture", "incise", "ablate", "select", etc. According to a preferred embodiment, a vocal command could be one or more complex sentences.

The term "surgical mask" refers hereinafter to a protective mask intended to be worn by a surgeon/operating staff in a surgical setting to catch the bacteria shed in liquid droplets and aerosols from the wearer's mouth and nose.

The term "plurality" interchangeably refers hereinafter to an integer n, where n>1.

The term "qualifier" refers hereinafter to a vocal utterance that modifies a vocal command. Non-limiting examples include an amount, a selector and any combination thereof.

The term "amount" refers hereinafter to a value to be used to modify a vocal command. An amount can be a fraction of a value, e.g., a fraction of the size of a field of view, a fraction of a level of illumination, a fraction of an existing temperature, etc., or a fixed amount, such as a specified distance (e.g., in cm or mm), a specified amount of change in a lighting level (e.g., in lux or candela), a specified temperature change (e.g., in degrees C. or degrees F.).

The term 'tool', 'surgical tool' or 'surgical instrument' refers hereinafter to any instrument or device introducible into the human body. The term can refer to any location on the tool. For example it can refer to the tip of the same, the body of the same and any combination thereof. It should be further pointed that the following description can refer to a surgical tool/instrument as an endoscope.

The term "hazard" refers hereinafter to an object that can be damaged by an action, or which can damage an acting object. A non-limiting example of a hazard would be a tissue which could be damaged by a moving surgical tool.

The term "obstacle" refers hereinafter to an object which prevents an action from being carried out. Non-limiting examples of an obstacle include a tool which blocks the path of a moving tool, or a robotic arm that blocks the path of another moving robotic arm.

The term 'region of interest' refers hereinafter to any region within the human body which can be of interest to the operator of the system of the present invention. The region of interest can be, for example, an organ to be operated on, a restricted area to which approach of a surgical instrument is restricted, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof.)

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'automated assistant' refers hereinafter to any mechanical device (including but not limited to a robotic device) that can maneuver and control the position of a surgical or endoscopic instrument, and that can in addition be configured to receive commands from a remote source.

The term 'tool', "surgical tool" or 'surgical instrument' refers hereinafter to any instrument or device introducible into the human body. The term can refer to any location on the tool. For example it can refer to the tip of the same, the body of the same and any combination thereof. It should be further pointed that the following description can refer to a surgical tool/instrument as an endoscope.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'allowed' refers hereinafter to any action which is permitted according to a predetermined set of rules.

The term 'restricted' refers hereinafter to any action which is forbidden according to a predetermined set of rules. For example, for an apparatus comprising a maneuvering subsystem, one rule, provides a preferred volume zone rule which defines a favored zone within a surgical environment. Thus, according to the present invention an allowed movement of a surgical tool or the endoscope is a movement which maintains the surgical tool within the favored zone; and a restricted movement of a surgical tool is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps. The term "about" refers hereinafter to 20% more or less than the defined value.

Figure 1B:
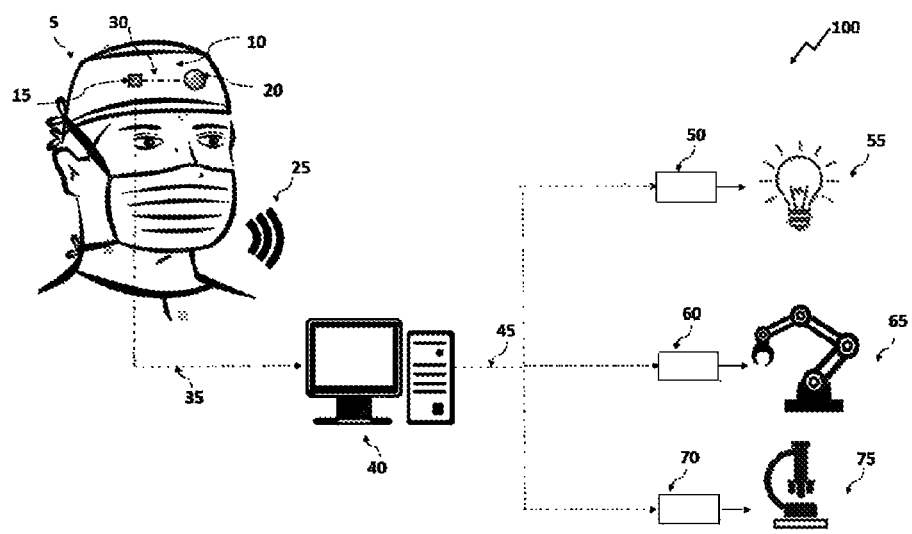

Reference is now made to FIGS. 1a-1b schematically illustrating an embodiment of the vocally activated control system (100), in an out of scale manner.

In FIG. 1a, the vocally activated control system (100) includes a voice sensor (20) configured to detect one or more vocal commands (25) that are generated by a surgeon/operating staff (5) in a surgical setting. A vocal command could be a simple phrase such as, but not limited to, "on", "off", "zoom in", "zoom out", "left", "right", "up", "down", "start", "stop", "increase", "decrease", "open", "close", "suture", "incise", "ablate", "select", a complex phrase such as, but not limited to "left 10%", a complex sentence, and any combination thereof. According to some preferred embodiments, the vocal command is preceded by at least one activation word such as, but not limited to, "system on", to activate the system (100). Each vocal command (25) is pre-assigned with at least one predetermined set of rules such that, when the vocal command is detected by the voice sensor (20), the predetermined set of rules generates a set of instructions carried out by corresponding apparatus. The vocally activated control system (100) is used to control a plurality of apparatus in the surgical setting, such as, but not limited to, endoscope, microscope, robotic arm, laparoscopy, operating light, surgical table, surgical camera, imaging device, injection device, measurement device, optical device, stereotactic device, positioning device, suction device, sealing device, ablation means, resection means, dissection means and any combination thereof.

A simple phrase can initiate a complex set of predetermined commands For non-limiting example, the vocal command "suture" will induce complex movements of at least two forceps, a thread-cutting instrument, and possibly graspers or retractors as well.

According to some preferred embodiment, the voice sensor (20) comprises a microphone configured to pick up a plurality of vocal command and a voice recognition unit performing a vocal recognition algorithm on the vocal command picked up by the microphone thereby recognize the vocal command and generate a set of command output signals to be received by the signal transmitter (15). The vocal recognition algorithm could be based on hidden markov model, dynamic time warping, neural networks, deep neural networks and any combination thereof. Such voice recognition units can be found in the art and are readily available. When a vocal command is a complex sentence, the voice sensor (20), a processor and any combination thereof further comprises a context recognition unit configured to recognize the vocal command from the complex sentence. According to a preferred embodiment, the voice sensor (20) is set up or trained in a fixed position relative to a surgeon's mouth and is adjusted for optimal performance with the audio signal components thereby produced. For an utterance by a surgeon, the voice signal detected by the voice sensor can have different compositions depending on its position relative to the surgeon's mouth. For reliable voice recognition results, especially in environments where safety is of the utmost concern, the voice sensor should be positioned in a fixed and repeatable location relative to the surgeon's mouth.

With continued reference to FIG. 1a, the voice sensor (20) is operatively connected to a signal transmitter (15). In some embodiments, the connection is via a wireless means (30) such as, but not limited to, a Bluetooth device. According to a preferred embodiment, the voice sensor (20) is connected to the signal transmitter (15) via wired means such as an electric cable. The signal transmitter (15) is configured to convert said at least one vocal command into a transmittable vocal signal and then transmit the transmittable vocal signal. According to some preferred embodiments, the signal transmitter (15) is RFID, digital RF, RF Communication, an IR emitter, a Bluetooth device and any combination thereof.

Both the voice sensor (20) and the signal transmitter (15) are integrated with the surgical mask (10) worn by the surgeon in the surgical setting. The voice sensor is positioned in the proximity of the surgeon's mouth. According to a preferred embodiment, both the voice sensor (20) and the signal transmitter (15) are embedded in the surgical mask. According to another preferred embodiment, they are reversibly embedded in the mask and can be removed from one surgical mask and placed onto/into another surgical mask. According to some embodiment, the surgical mask is disposable. According to some other embodiment, the surgical mask is reusable.

With yet continued reference to FIG. 1a, the vocally activated control system (100) further comprises a processor (40) operatively connected to the signal transmitter (15) and configured to receive the transmittable vocal signal. The processor is connected to the signal transmitter in a wired or wireless manner (35). The processor is configured to convert the transmittable vocal signal to at least one predetermined set of rules which generates at least one set of operative instructions, where the set of operative instructions comprises at least one operative instruction associated with operation of at least one of a plurality of apparatus, such as, but not limited to, an operating light (55), a robotic arm (65), a surgical microscope (75) and any combination thereof. Each apparatus can responds to at least one predetermined set of instructions via a control means (50, 60 and 70) associated with each apparatus, where a predetermined set of instructions comprises at least one instruction. Each control means is a controller operatively connected to the processor (40) and to the apparatus it controls (55, 65 and 75). The control means are configured to receive at least one predetermined set of instructions and to cause the apparatus to operate accordingly. According to a preferred embodiment, the processor (40) further comprises a storage unit for storing a database of transmittable vocal signals. The database can be constantly updated and personalized according to different user preferences.

According to a preferred embodiment, the vocally activated control system (100) further comprises a feedback mechanism that facilitates direct communication between a surgeon and the system. According to some embodiments, the feedback mechanism is configured to transmit audio or visual signals. Non-limiting example of such signals include: affirming operative instructions are properly carried out, audio signals indicating the vocal command was not clearly received, etc. Non-limiting examples of an audio feedback mechanism include an earpiece, a headphone, a helmet, a neckpiece, a microphone and any combination thereof. Non-limiting examples of a visual feedback mechanism include a "heads-up" helmet providing a visual display, glasses configured to provide a visual display, a goggle configured to provide a visual display, a display screen and any combination thereof. The audio or visual feedback mechanism can be attachable to a surgeon, attachable to apparatus in the surgical environment, integrated into the system, and any combination thereof.

FIG. 1B illustrates the same system as illustrated in FIG. 1a, except that the voice sensor (20) and the signal transmitter (15) are integrated within a surgical cap (10) worn by the surgeon.

It should be emphasized that a voice sensor (20) and signal transmitter (15) can be attachable to or integrated within any wearable element. The element can selected from a group consisting of mask, helmet, headpiece, cap, shoe cover, glove\s, hospital robe, surgical garb, gown, neckpiece, wristlet, armlet, earpiece and any combination thereof. The attachment can be reversible or irreversible. In some embodiments, a voice sensor can be either reversibly or irreversibly attachable to apparatus or integrated into apparatus, or they can be either reversibly or irreversibly attached to the system or be an integral part of the system. Preferably, there is one a voice sensor (20) and signal transmitter (15) per surgeon; however, in some embodiments, at least one surgeon has a plurality of a voice sensor (20) and signal transmitter (15). In some embodiments, at least one voice sensor (20) and signal transmitter (15) is configured to sense vocal commands from a plurality of surgeons. For non-limiting example, a voice sensors (20) can be configured to receive vocal commands from a plurality of surgeons (multiple-surgeon sensor); the interpreted voice commands for a multiple-surgeon sensor can then be correlated with voice commands from an individual surgeon's voice sensor (20), thus acting as a check on the received commands In another non-limiting example, a multiple-surgeon sensor can be used as backup—if a surgeon's individual voice sensor (20) fails, commands received by the multiple-surgeon sensor can be used instead, thus preventing interruption of the flow of work in the operating environment.

Figure 2:
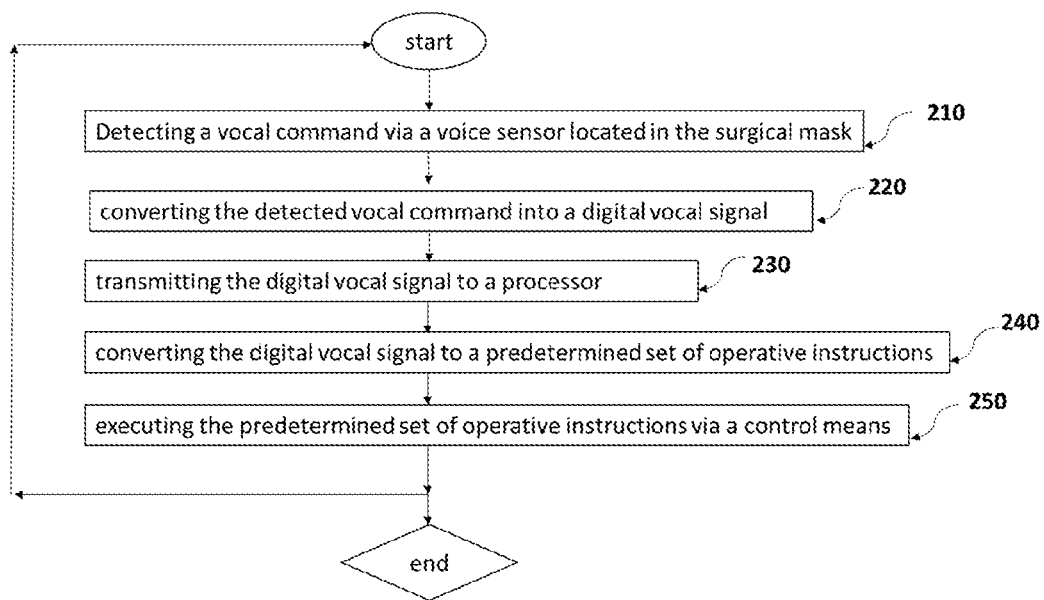
FIG. 2 is a flow chart showing the overall high level view of method of vocally activated control process according to a preferred embodiment of the present invention.

Reference is now made to FIG. 2, which presents a flow chart showing an overall high level view of a method for a vocally activated control process according to a preferred embodiment of the present invention. The surgeon/operating staff can start the vocally activated system using an activation phrase such as "system on" before a vocal command A voice sensor, embedded in a surgical mask worn by a surgeon/operating staff or otherwise positioned in proximity to the surgeon/operating staff detects a vocal command produced by the surgeon/operating staff (210). Afterwards, a signal transmitter operatively connected to the voice sensor converts the vocal command into a transmittable signal correlated with the vocal command (a transmittable vocal signal), preferably as a digital vocal signal (220) (less preferably, as an analog vocal signal) and transmits the transmittable vocal signal to a central processor (230). The central processor receives the transmittable vocal signal and converts it to a predetermined set of rules, comprising at least one rule associated with at least one apparatus. The set of rules generates at least one operative instruction associated with at least one apparatus such as an operating light, a robotic arm a surgical microscope (240) or any automatically controllable apparatus associatable with a surgical environment. A control means operatively connected to both processor and apparatus then executes the predetermined operative instructions accordingly (250). This process can be iterative or can be automatically disabled after completion of one set of instructions. If the process is iterative, it can be stopped with and ending phrase such as, but not limited to, "system off" or it can continue as long as the system is operative.

It is also within the scope of the present invention to disclose the system as described above, wherein, prior to use during a procedure, the system undergoes vocal training. During said vocal training, the system will be trained, by means well-known in the art, to identify vocal commands with the voice and pronunciation of at least one surgeon to which the same will have to respond.

A vocal command can be unqualified or can comprise at least one qualifier, where a qualifier modifies a component of a response. For non-limiting example, a qualifier can be an amount, either in fixed terms or as a fraction of a value. For a non-limiting example, the command "move left" will be used. A qualified command comprising a fraction could be "move left 20%", which could move a selected tool leftwards by 20% of the field of view; a surgical tool that was at the left edge of the field of view could, after the move, be 20% of the width of the field of view from the left edge of the field of view. A qualified command comprising a fixed-term value could be "move left 3 cm", which could move a surgical tool that was 3 cm to the right of the object at the center of the field of view before the command to the center of the field of view. Many more examples will be obvious to one skilled in the art.

In another non-limiting example, a qualifier can be a surgical tool or an apparatus. For non-limiting example, a command could be "move forceps left", which would move the forceps to the left, or "move endoscope left" which would move the field of view to the left. Many more examples will be obvious to one skilled in the art.

An unqualified command can comprise a predetermined qualifier or it can initiate a process which continues until stopped. The predetermined qualifier can be, as disclosed above, a fraction or a fixed-term value. As above, non-limiting examples will be provided for the command "move left". If the command is continued until stopped, a selected object would continue moving left until a command such as "stop move left" is issued. If the predetermined qualifier is a fraction, a command "move left" would move the object leftward for a fixed amount, such as moving left by 20% of the field of view. If the predetermined qualifier is a fixed-term value, a command "move left" would move the object leftward for a fixed amount, such as moving left by 3 cm. Many more examples will be obvious to one skilled in the art.

It should be noted that, in some embodiments, a vocal command can reversibly select (i.e., select or deselect) or apparatus, a surgical tool, at least a portion of a patient, and any combination thereof; a selected item can remain selected until a change command is received or can remain selected for a predetermined time.

In some embodiments, a vocal command can change a predetermined amount; the value can be changed, or the type of value can be changed, e.g., from a fixed-term value to a fraction or vice versa.

The set of predetermined commands can comprise a "dumb" response or a "smart" response to a vocal command In a dumb response, the command is executed as ordered. For non-limiting examples, in a dumb response, the command "move left" would move a selected surgical tool leftward, ignoring any hazards or obstacles in the surgical tool's path. A "zoom in" command could continue until the endoscope was pressing on tissue, or a "zoom out" command could continue until the endoscope had retreated into the trocar through which it was inserted into the body cavity.

A "smart" response, on the other hand, is configured to take into account at least one feature of the surrounding environment. The feature can be a hazard or obstacle, of a hazard or obstacle, an interference between two surgical tools, an interference between two parts of an apparatus, interference between two apparatus, possibility of damage to a portion of a patient, and any combination thereof. For non-limiting example, for a movement, a hazard or obstacle in the path, such as a surgical tool or tissue, could be taken into account. In such case, for non-limiting example, a command "move left 3 cm" would move a selected surgical tool 3 cm leftward, but the path need not be a straight line. The selected tool could move upward to avoid a second tool in its path, then move toward the patient's diaphragm and away from it to avoid the right lobe of the liver, with which it would otherwise come into contact. A "zoom in" command would automatically terminate, even if a desired zoom had not been completed, when an endoscope came closer to at least one of a hazard or obstacle than a predetermined distance. A "zoom out" command would automatically terminate, even if a desired level of zoom did not yet exist, even if a desired zoom had not been completed, when an endoscope was too far out, for non-limiting example, if a part of a trocar was visible, or the endoscope was likely to come into unwanted contact with an inlet port.

A command can be a "dumb" command or a "smart" command A dumb command executes a simple action, often requiring no smart response, whereas a smart command executes a more complex action, typically requiring at least one smart response.

An example of a dumb command is adjusting lighting. A command "lighting on" turns on a light source. A command "brighter light" increases brightness by a predetermined amount. Similarly, "lighting off" would turn the light source off, while "dimmer light" would decrease brightness.

An example of a smart command is the vocal command "suture", which can include a set of rules which generate the instructions which will move forceps to pierce tissue and pass a thread through the tissue, move forceps to tie a knot in the thread, and cut the thread using a cutting instrument. The rules would preferably include rules to avoid hazards or obstacles in the paths of the instruments. In some embodiments, a set of rules generates instructions to move the forceps (and/or cutting instrument) to the site of a suture. In some embodiments, a set of rules generates instructions and to move the forceps (and/or cutting instrument) away from the site of the suture after the suture is completed.

A more complex smart command could be "close incision", which would comprise rules to automatically generate instructions to close an incision with a series of sutures.

The system can include, for example, rules and predetermined sets of to control apparatus such as an endoscope, a microscope, a robotic arm, laparoscopy, operating light, surgical table, surgical camera, imaging device, injection device, measurement device, optical device, stereotactic device, positioning device, suction device, sealing device, ablation means, resection means, dissection means and any combination thereof.

Thus, according to a preferred embodiment of the present invention, the present invention provides, for a surgical tool, a predetermined set of rules which define what is an "allowed action" of at least one surgical tool within the surgical environment and what is a "restricted action" of at least one surgical tool within the surgical environment.

For other apparatus, other predetermined rules can be supplied, for non-limiting example, for a surgical table, a rule can determine the at least one instruction which adjusts the height of the table, speed of movement of the table, tilt of the table, etc.

For illumination, rules can determine the instruction which adjust on/off state, color, brightness, etc.

For an optical device, the rules can determine focus, field of view, depth of field, still or video action, etc.

The system can prevent a restricted action, can merely provide an alert of a restricted action instead of preventing it, and any combination thereof.

According to some embodiments, the system of the present invention comprises a maneuvering subsystem communicable with the controller, the maneuvering subsystem is configured to spatially reposition the at least one surgical tool during surgery according to the predetermined set of rules.

According to some embodiments, the controller can provide instructions to a maneuvering subsystem for spatially repositioning the location of the surgical tool. According to these instructions, only an allowed movement of the surgical tool would be performed. Preventing a restricted movement is performed by: detecting the location of the surgical tool; processing all current rules; analyzing the movement of the surgical tool and preventing the movement if the tool's movement is a restricted movement.

According to some embodiments, system merely alerts the physician of a restricted movement of at least one surgical tool (instead of preventing said restricted movement).

Alerting the physician of a restricted movement (or, alternatively preventing a restricted movement) is performed by: detecting the location of the surgical tool; processing all current rules; analyzing the movement of the surgical tool and informing the surgeon (the user of the system) if the tool's movement is an allowed movement or a restricted movement.

Thus, according to a preferred embodiment of the present invention, if restricted movements are prevented, the same process (of detecting the location of the surgical tool; processing all current rules and analyzing the movement of the surgical tool) is followed except for the last movement, where the movement is prevented if the tool's movement is a restricted movement. The surgeon can also be informed that the movement is being prevented.

According to some embodiments, the above (alerting the physician and/or preventing the movement) is performed by detecting the location of the surgical tool and analyzing the surgical environment of the surgical tool. Following analysis of the surgical environment and detection of the location of the surgical tool, the system can assess all the risks which can follow a movement of the surgical tool in the predetermined direction. Therefore, each location in the surgical environment has to be analyzed so that any possible movement of the surgical tool will be classified as an allowed movement or a restricted movement.

According to one embodiment of the present invention, the location of each tool is determined using image processing means and determining in real-time what is the 3D spatial location of each tool. It should be understood that the above mentioned "tool" can refer to the any location on the tool. For example, it can refer to the tip of the same, the body of the same and any combination thereof. The predetermined set of rules which generate the instructions are configured to take into consideration all the possible factors which can be important during a surgical procedure. The predetermined set of rules can comprise the following rules or any combination thereof:

a. a route rule;
b. an environment rule;
c. an operator input rule;
d. a proximity rule;
e. a tagged tool rule;
f. a collision prevention rule;
g. a history based rule;
h. a tool-dependent allowed and restricted movement rule.
i. a most used tool rule;
j. a right tool rule;
k. a left tool rule;
l. a field of view rule;
m. a no fly zone rule;
n. an operator input rule;
a preferred volume zone rule;
p. a preferred tool rule;
q. a movement detection rule;
r. a tagged tool rule;
s. a preferred tool rule;
t. a change of rule and
u. a go-to rule.

Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a restricted movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and its functions:

According to some embodiments, the route rule comprises a predefined route in which the at least one surgical tool is configured to move within the surgical environment; an allowed movement is a movement in which the at least one surgical tool is located within the borders of the predefined route, and a restricted movement is a movement in which the at least one surgical tool is located out of the borders of the predefined route. Thus, according to this embodiment, the route rule comprises a communicable database storing at least one predefined route in which the at least one surgical tool is configured to move within the surgical environment; the predefined route comprises n 3D spatial positions of the at least one surgical tool in the route; n is an integer greater than or equal to 2; an allowed movement is a movement in which the at least one surgical tool is located substantially in at least one of the n 3D spatial positions of the predefined route, and a restricted movement is a movement in which the location of the at least one surgical tool is substantially different from the n 3D spatial positions of the predefined route.

In other words, according to the route rule, each of the surgical tool's courses (and path in any surgical procedure) is stored in a communicable database. An allowed movement is defined as a movement in which the at least one surgical tool is located substantially in at least one of the stored routes; and a restricted movement is movement in which the at least one surgical tool is in a substantially different location than any location in any stored route.

According to some embodiments, the environmental rule is configured to determine allowed and restricted movement according to hazards or obstacles in the surgical environment as received from an endoscope or other sensing means. Thus, according to this embodiment, the environmental rule comprises a comprises a communicable database; the communicable database is configured to received real-time images of the surgical environment and is configured to perform real-time image processing of the same and to determine the 3D spatial position of hazards or obstacles in the surgical environment; the environmental rule is configured to determine allowed and restricted movement according to the hazards or obstacles in the surgical environment, such that a restricted movement is a movement in which at least one surgical tool is located substantially in at least one of the 3D spatial positions, and an allowed movement is a movement in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. A restricted movement is defined as a movement in which the at least one surgical tool is located substantially in the same location as that of a hazard or obstacle; and an allowed movement is a movement in which the location of the at least one surgical tool is substantially different from that of all of the hazards or obstacles.

According to other embodiments, a hazards or obstacle in the surgical environment is selected from a group consisting of a tissue, a surgical tool, an organ, an endoscope and any combination thereof.

According to some embodiments, the operator input rule is configured to receive an input from the operator of the system regarding allowed and restricted movement of the at least one surgical tool. Thus, according to this embodiment, the operator input rule comprises a communicable database; the communicable database is configured to receive an input from the operator of the system regarding allowed and restricted movement of the at least one surgical tool.

According to other embodiments, the input comprises n 3D spatial positions; n is an integer greater than or equal to 2; wherein at least one of which is defined as an allowed location and at least one of which is defined as a restricted location, such that an allowed movement is a movement in which the at least one surgical tool is located substantially in at least one of the n 3D allowed spatial positions, and a restricted movement is a movement in which the location of the at least one surgical tool is substantially different from the n 3D allowed spatial positions.

According to other embodiments, the input comprises at least one rule according to which an allowed and a restricted movement of the at least one surgical tool can be determined, such that the spatial position of the at least one surgical tool is controlled by the controller according to the allowed and restricted movements.

According to other embodiments, the operator input rule can convert an allowed movement to a restricted movement and a restricted movement to an allowed movement.

According to some embodiments, the proximity rule is configured to define a predetermined distance between the at least one surgical tool and at least one another surgical tool; an allowed movement is a movement in which the surgical tool is within the range or out of the range of the predetermined distance, and a restricted movement in which the surgical tool is out of the range or within the range of the predetermined distance; an allowed movement and a restricted movement can be defined according to different ranges. Thus, according to this embodiment, the proximity rule is configured to define a predetermined distance between at least two surgical tools. In a preferred embodiment, an allowed movement is a movement in which the surgical tool is within the range of the predetermined distance, while a restricted movement is a movement in which the surgical tool is out of the range of the predetermined distance. In another preferred embodiment, an allowed movement is a movement in which the surgical tool is out of the range of the predetermined distance, while a restricted movement is a movement in which the surgical tool within the range of the predetermined distance.

It should be pointed out that the above mentioned distance can be selected from the following:
(a) the distance between the tip of the first tool and the tip of the second tool;
(b) the distance between the body of the first tool and the tip of the second tool;
(c) the distance between the body of the first tool and the body of the second tool;
(d) the distance between the tip of the first tool and the body of the second tool; and any combination thereof.

According to some embodiments, the proximity rule is configured to define a predetermined angle between at least two surgical tools; an allowed movement is a movement in which the surgical tool is within the range or out of the range of the predetermined angle, and a restricted movement is a movement in which the surgical tool is out of the range or within the range of the predetermined angle.

According to some embodiments, the collision prevention rule is configured to define a predetermined distance between the at least one surgical tool and an anatomical element within the surgical environment (e.g. tissue, organ, another surgical tool or any combination thereof); an allowed movement is a movement in which the surgical tool is in a range that is larger than the predetermined distance, and a restricted movement is a movement in which the surgical tool is in a range that is smaller than the predetermined distance.

According to some embodiments, the anatomical element is selected from a group consisting of tissue, organ, another surgical tool or any combination thereof.

According to some embodiments, the surgical tool is an endoscope. The endoscope is configured to provide real-time images of the surgical environment.

According to some embodiments, the right tool rule is configured to determine the allowed movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A restricted movement, according to the right tool rule, is a movement in which the endoscope field of view is moved to a location substantially different from the location of the right tool.

According to some embodiments, the left tool rule is configured to determine the allowed movement of the endoscope according to the movement of a surgical tool in a specified position in relation to the endoscope, preferably positioned to left of the same. According to this rule, the tool which is defined as the left tool is constantly tracked by the endoscope. According to some embodiments, the left tool is defined as the tool positioned to the left of the endoscope; according to other embodiments, any tool can be defined as the left tool. An allowed movement, according to the left tool rule, is a movement in which the endoscope field of view is moved to a location substantially the same as the location of the left tool. A restricted movement, according to the left tool rule, is a movement in which the endoscope field of view is moved to a location substantially different from the location of the left tool.

According to some embodiments, the field of view rule is configured to define a field of view and maintain that field of view. The field of view rule is defined such that if the endoscope is configured to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is configured to determine the allowed movement of the endoscope within the n 3D spatial positions so as to maintain a constant field of view, such that the allowed movement is a movement in which the endoscope is located substantially in at least one of the n 3D spatial positions, and a restricted movement is a movement in which the location of the endoscope is substantially different from the n 3D spatial positions.

Thus, according to some embodiments of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spatial locations of the same, where m is an integer greater than or equal to 1 and where a tool can be a surgical tool, an anatomical element and any combination thereof. The combination of all of then 3D spatial positions provides a predetermined field of view. The field of view rule is configured to determine allowed movement of the endoscope such that the m 3D spatial positions of the tools comprise at least one of the n 3D spatial positions of the field of view, and a restricted movement is a movement in which the 3D spatial position of at least one tool is substantially different from the n 3D spatial positions of the field of view.

According to some embodiments, the preferred volume zone rule comprises a communicable database comprising n 3D spatial positions; n is an integer greater than or equal to 2; the n 3D spatial positions provides the preferred volume zone; the preferred volume zone rule is configured to determine the allowed movement of a surgical tool within the n 3D spatial positions and restricted movement of the surgical tool outside the n 3D spatial positions, such that an allowed movement is a movement in which the surgical tool is located substantially in at least one of the n 3D spatial positions, and a restricted movement is a movement in which the location of the surgical tool is substantially different from the n 3D spatial positions. In other words, the preferred volume zone rule defines a volume of interest (a desired volume of interest), such that an allowed movement, according to the preferred volume zone rule, is a movement in which at least a portion of the surgical tool is moved to a location within the defined preferred volume. A restricted movement, according to the preferred volume zone rule, is a movement in which all of the surgical tool is moved to a location outside the defined preferred volume.

According to some embodiments, the preferred tool rule comprises a communicable database, the database stores a preferred tool; the preferred tool rule is configured to determine the allowed movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the endoscope is moved to a location substantially the same as the location of the preferred tool. A restricted movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user can define in said preferred tool rule to constantly tack the tip of said preferred tool or alternatively, the user can define in said preferred tool rule to constantly track the body or any location on the preferred tool.

According to some embodiments, the no fly zone rule is configured to define a restricted zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is configured to determine a restricted movement if the movement is within the no fly zone and an allowed movement if the movement is outside the no fly zone, such that a restricted movement is a movement in which the at least one surgical tool is located substantially in at least one of the n 3D spatial positions, and an allowed movement is a movement in which the location of the at least one surgical tool is substantially different from the n 3D spatial positions.

According to some embodiments, the most used tool function is configured to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is configured to constantly position the endoscope to track the movement of the surgical tool with the largest number of movements. In some embodiments of the most used tool function, the communicable database measures the amount of movement of each of the surgical tools; the most used tool rule is configured to constantly position the endoscope to track the movement of the surgical tool with the largest amount of movement.

According to some embodiments, the system is configured to alert the physician of a restricted movement of at least one surgical tool. The alert can be audio signaling, voice signaling, light signaling, flashing signaling and any combination thereof.

According to some embodiments, an allowed movement is one permitted by the controller and a restricted movement is one denied by the controller.

According to some embodiments, the operator input rule function is configured to receive an input from the operator of the system regarding an allowed movement and a restricted movement of the at least one surgical tool. In other words, the operator input rule function receives instructions from the physician as to what can be regarded as an allowed movement and what is a restricted movement. According to some embodiments, the operator input rule is configured to convert an allowed movement to a restricted movement and a restricted movement to an allowed movement.

According to some embodiments, the history-based rule is configured to determine the allowed and restricted movement according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is configured to determine an allowed movement and a restricted movement according to historical movements of the at least one surgical tool, such that an allowed movement is a movement in which the at least one surgical tool is located substantially in at least one of the 3D spatial positions, and a restricted movement is a movement in which the location of the at least one surgical tool is substantially different from the n 3D spatial positions.

According to some embodiments, the tool-dependent allowed and restricted movement rule is configured to determine allowed and restricted movement according to predetermined characteristics of the surgical tool, where a predetermined characteristic of a surgical tool is selected from a group consisting of: physical dimensions, structure, weight, sharpness, and any combination thereof. Thus, according to this embodiment, the tool-dependent allowed and restricted movement rule comprises a communicable database; the communicable database is configured to store predetermined characteristics of at least one of the surgical tools; the tool-dependent allowed and restricted movement rule is configured to determine an allowed and a restricted movement according to the predetermined characteristics of the surgical tool.

According to some embodiments, a predetermined characteristic of the surgical tool can be selected from a group consisting of: physical dimensions, structure, weight, sharpness, and any combination thereof.

According to these embodiments, the user can define, e.g., the structure of the surgical tool he wishes the endoscope to track. Thus, according to the tool-dependent allowed and restricted movement rule the endoscope constantly tracks the surgical tool having said predetermined characteristics as defined by the user.

According to some embodiments of the present invention, the movement detection rule comprises a communicable database comprising the real-time 3D spatial positions of each surgical tool; said movement detection rule is configured to detect movement of at least one surgical tool. When a change in the 3D spatial position of that surgical tool is received, allowed movement is a movement in which the endoscope is re-directed to focus on the moving surgical tool.

According to some embodiments, the change of speed rule is configured to automatically vary the speed of a predetermined location on a surgical tool based on the predetermined location's distance from an object, be it a tool, an obstacle, or the object of interest. Typically, the speed is varied such that, the closer the predetermined location on the surgical tool is to the object, the more slowly the surgical tool moves. It should be noted that the predetermined location can be a functional part of a surgical tool, such as, but not limited to, a location on a blade of a cutter or a location on a face of a grasper.

According to some embodiments of the present invention, the go-to rule moves a predetermined object to a predetermined location. For example, an endoscope can be re-directed to focus on at least one predetermined location, a tagged tool can be re-directed to position at least a portion of the tagged tool on at least one predetermined location, and any combination thereof.

According to some embodiments, the at least one location estimator is at least one endoscope configured to acquire at least one real-time image of a surgical environment within the human body for the estimation of the location of at least one surgical tool and at least one surgical instrument spatial location software configured to receive the at least one real-time image of the surgical environment and to estimate the 3D spatial position of the at least one surgical tool.

According to some embodiments, the location estimator comprise at least one selected from a group consisting of optical imaging means, radio frequency transmitting and receiving means, at least one mark on at least one surgical tool and any combination thereof.

According to some embodiments, the at least one location estimator is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm configured to record images received by each camera of each of the M cameras and to calculate therefrom the position of each of the tools, and further configured to provide automatically the results of the calculation to the human operator of the interface.

The system can comprise a "smart" tracking subsystem, which receives instructions from a maneuvering function f(t) (t is the time) as to where to direct the endoscope and which instructs the maneuvering subsystem to relocate the endoscope to the required area.

The maneuvering function f(t) receives, as input, output from at least two instructing functions gi(t), analyses their output and provides instruction to the "smart" tracking system (which eventually re-directs the endoscope).

According to some embodiments, each instructing function gi(t) is also given a weighting function, αi(t).

The instructing functions gi(t) of the present invention are functions which are configured to assess the environment of the endoscope and the surgery, and to output data which guides the tracking subsystem for controlling the spatial position of the maneuvering subsystem and the endoscope. The instructing functions gi(t) can be selected from a group consisting of:

a. a tool detection function g1(*t*);
b. a movement detection function g2(*t*);
c. an organ detection function g3(*t*);
d. a collision detection function g4(*t*);
e. an operator input function g5(*t*);
f. a prediction function g6(*t*);
g. a past statistical analysis function g7(*t*);
h. a most used tool function g8(*t*);
i. a right tool function g9(*t*);
j. a left tool function g10(*t*);
k. a field of view function g11(*t*);
l. a preferred volume zone function g12(*t*);
m. a no fly zone function g13(*t*);
n. a proximity function g14(*t*);
o. a tagged tool function g15(*t*);
p. a preferred tool function g16(*t*);
q. a change of speed function g17(*t*) and
r. a go-to function g18(*t*).

Thus, for example, the maneuvering function f(t) receives input from two instructing functions: the collision detection function g4(*t*) (the function providing information whether the distance between two elements is smaller than a predetermined distance) and from the most used tool function g8(*t*) (the function counts the number of times each tool is moved during a surgical procedure and provides information as to whether the most moved or most used tool is currently moving). The output given from the collision detection function g4(*t*) is that a surgical tool is dangerously close to an organ in the surgical environment. The output given from the most used tool function g8(*t*) is that the tool identified statistically as the most moved tool is currently moving.

The maneuvering function f(t) then assigns each of the instructing functions with weighting functions $\alpha i(t)$. For example, the most used tool function $g8(t)$ is assigned with a greater weight than the weight assigned to the collision detection function $g4(t)$.

After the maneuvering function f(t) analyses the information received from the instructing functions gi(t) and the weighting functions $\alpha i(t)$ of each, the same outputs instructions to the maneuvering subsystem to re-direct the endoscope (either to focus on the moving tool or on the tool approaching dangerously close to the organ).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

According to some embodiments, the surgical tracking subsystem comprises:
  a. at least one endoscope configured to acquire real-time images of a surgical environment within the human body;
  b. a maneuvering subsystem configured to control the spatial position of the endoscope during the laparoscopic surgery; and
  c. a tracking subsystem in communication with the maneuvering subsystem, configured to control the maneuvering subsystem so as to direct and modify the spatial position of the endoscope to a region of interest.

According to this embodiment, the tracking subsystem comprises a data processor. The data processor is configured to perform real-time image processing of the surgical environment and to instruct the maneuvering subsystem to modify the spatial position of the endoscope according to input received from a maneuvering function f(t); the maneuvering function f(t) is configured to (a) receive input from at least two instructing functions gi(t), where i is 1, . . . , n and n≥2 and where t is time; i and n are integers; and (b) to output instructions to the maneuvering subsystem based on the input from the at least two instructing functions gi(t), so as to spatially position the endoscope to the region of interest.

According to one embodiment, the tool detection function $g1(t)$ is configured to detect tools in the surgical environment. According to this embodiment, the tool detection function is configured to detect surgical tools in the surgical environment and to output instructions to the tracking subsystem to instruct the maneuvering subsystem to direct the endoscope to the detected surgical tools.

According to some embodiments, the functions gi(t) can rank the different detected areas in the surgical environment according to a ranking scale (e.g., from 1 to 10) in which a prohibited area (i.e., an area which is defined as an area into which at least one surgical tool is forbidden to enter) receive the lowest score (e.g., 1) and a preferred areas (i.e., an area which are defined as an area in which at least a portion of at least one surgical tool should be maintained) receive the highest score (e.g., 10).

According to a preferred embodiment, one function $g1(t)$ is configured to detect at least one tool in the surgical environment and inform the maneuvering function f(t) if I is in a preferred area or in a prohibited area.

According to some embodiments, the movement detection function $g2(t)$ comprises a communicable database comprising the real-time 3D spatial positions of each of the surgical tools in the surgical environment; means to detect movement of the at least one surgical tool when a change in the 3D spatial positions is received, and means to output instructions to the tracking subsystem to instruct the maneuvering subsystem to direct the endoscope to the moved surgical tool.

According to some embodiments, the organ detection function $g3(t)$ is configured to detect physiological organs in the surgical environment and to classify the detected organs as prohibited areas or preferred areas. For example, if the operator instructs the system that the specific surgery is kidney surgery, the organ detection function $g3(t)$ will classify the kidneys (or one kidney, if the surgery is specified to be on a single kidney) as a preferred area and other organs will be classified as prohibited areas. According to some embodiments, the organ detection function is configured to detect organs in the surgical environment and to output instructions to the tracking subsystem to instruct the maneuvering subsystem to direct the endoscope to the detected organs. According to some embodiments, the right tool function is configured to detect surgical tool positioned to right of the endoscope and to output instructions to the tracking subsystem to instruct the maneuvering system to constantly direct the endoscope on the right tool and to track the right tool.

According to some embodiments, the left tool function is configured to detect surgical tool positioned to left of the endoscope and to output instructions to the tracking subsystem to instruct the maneuvering system to constantly direct the endoscope on the left tool and to track the left tool.

According to some embodiments, the collision detection function $g4(t)$ is configured to detect prohibited areas within the surgical environment so as to prevent collisions between the endoscope and the prohibited areas. For example, if the endoscope is located in a narrow area in which a precise movement of the same is preferred, the collision detection function $g4(t)$ will detect and classify different areas (e.g., nerves, veins, walls of organs) as prohibited areas. Thus, according to this embodiment, the collision prevention function is configured to define a predetermined distance between the at least one surgical tool and an anatomical element within the surgical environment; and to output instructions to the tracking subsystem to instruct the maneuvering subsystem to direct the endoscope to the surgical tool and the anatomical element within the surgical environment if the distance between the at least one surgical tool and an anatomical element is less than the predetermined distance. According to one embodiment of the present invention the anatomical element is selected from a group consisting of tissue, organ, another surgical tool and any combination thereof.

According to some embodiments, the operator input function $g5(t)$ is configured to receive an input from the operator. The input can be, for example: an input regarding prohibited areas in the surgical environment, an input regarding allowed areas in the surgical environment, or an input regarding the region of interest and any combination thereof. The operator input function $g5(t)$ can receive instructions from the operator before or during the surgery, and respond accordingly. According to some embodiments, the operator input function can further comprise a selection algorithm for selection of areas selected from a group consisting of: prohibited areas, allowed areas, regions of interest, and any combination thereof. The selection can be performed via an input device (e.g., a touch screen).

According to some embodiments, the operator input function $g5(t)$ comprises a communicable database; the communicable database is configured to receive an input from the operator of the system; the input comprising n 3D spatial positions; n is an integer greater than or equal to 2; and to output instructions to the tracking subsystem to instruct the maneuvering subsystem to direct the endoscope to the at least one 3D spatial position received.

According to some embodiments, the prediction function g6(t) is configured to provide data regarding a surgical environment at a time tf>t0, wherein t0 is the present time and tf is a future time. The prediction function g6(t) can communicate with a database which stores data regarding the environment of the surgery (e.g., the organs in the environment). This data can be used by the prediction function g6(t) for the prediction of expected or unexpected events or expected or unexpected objects during the operation. Thus, according to this embodiment, the prediction function g6(t) comprises a communicable database storing each 3D spatial position of each of surgical tool within the surgical environment, such that each movement of each surgical tool is stored; the prediction function is configured to (a) to predict the future 3D spatial position of each of the surgical tools (or each object); and, (b) to output instructions to the tracking subsystem to instruct the maneuvering subsystem to direct the endoscope to the future 3D spatial position.

According to some embodiments, the past statistical analysis function g7(t) is configured to provide data regarding the surgical environment or the laparoscopic surgery based on past statistical data stored in a database. The data regarding the surgical environment can be for example: data regarding prohibited areas, data regarding allowed areas, data regarding the region of interest and any combination thereof. Thus, according to this embodiment, the past statistical analysis function g6(t) comprises a communicable database storing each 3D spatial position of each of surgical tool within the surgical environment, such that each movement of each surgical tool is stored; the past statistical analysis function g6(t) is configured to (a) perform statistical analysis on the 3D spatial positions of each of the surgical tools in the past; and, (b) to predict the future 3D spatial position of each of the surgical tools; and, (c) to output instructions to the tracking subsystem to instruct the maneuvering subsystem to direct the endoscope to the future 3D spatial position. Thus, according to the past statistical analysis function g7(t), the past movements of each tool are analyzed and, according to this analysis, a prediction of the tool's next move is provided.

According to some embodiments, the most used tool function g8(t) comprises a communicable database counting the amount of movement of each surgical tool located within the surgical environment; the most used tool function is configured to output instructions to the tracking subsystem to instruct the maneuvering subsystem to direct the endoscope to constantly position the endoscope to track the movement of the most moved surgical tool. The amount of movement of a tool can be defined as the total number of movements of that tool or the total distance the tool has moved.

According to some embodiments, the right tool function g9(t) is configured to detect at least one surgical tool in a specified position in relation to the endoscope, preferably positioned to right of the endoscope and to output instructions to the tracking subsystem to instruct the maneuvering subsystem to constantly direct the endoscope to the right tool and to track the same. According to preferred embodiments, the right tool is defined as the tool positioned to the right of the endoscope; according to other embodiments, any tool can be defined as the right tool.

According to some embodiments, the left tool function g10(t) is configured to detect at least one surgical tool in a specified position in relation to the endoscope, preferably positioned to left of the endoscope and to output instructions to the tracking subsystem to instruct the maneuvering subsystem to constantly direct the endoscope to the left tool and to track the same. According to preferred embodiments, the left tool is defined as the tool positioned to the left of the endoscope; according to other embodiments, any tool can be defined as the left tool.

According to some embodiments, the field of view function g11(t) comprises a communicable database comprising n 3D spatial positions; n is an integer greater than or equal to 2; the combination of all of the n 3D spatial positions provides a predetermined field of view; the field of view function is configured to output instructions to the tracking subsystem to instruct the maneuvering subsystem to direct the endoscope to at least one 3D spatial position substantially within the n 3D spatial positions so as to maintain a constant field of view.

According to some embodiments, the preferred volume zone function g12(t) comprises a communicable database comprising n 3D spatial positions; n is an integer greater than or equal to 2; the n 3D spatial positions provide the preferred volume zone; the preferred volume zone function g12(t) is configured to output instructions to the tracking subsystem to instruct the maneuvering subsystem to direct the endoscope to at least one 3D spatial position substantially within the preferred volume zone.

According to some embodiments, the no fly zone function g13(t) comprises a communicable database comprising n 3D spatial positions; n is an integer greater than or equal to 2; the n 3D spatial positions define a predetermined volume within the surgical environment; the no fly zone function g13(t) is configured to output instructions to the tracking subsystem to instruct the maneuvering subsystem to direct the endoscope to at least one 3D spatial position substantially different from all the n 3D spatial positions.

According to some embodiments, the proximity function g14(t) is configured to define a predetermined distance between at least two surgical tools; and to output instructions to the tracking subsystem to instruct the maneuvering subsystem to direct the endoscope to the two surgical tools if the distance between the two surgical tools is less than or if it is greater than the predetermined distance.

According to some embodiments, the proximity function g14(t) is configured to define a predetermined angle between at least two surgical tools; and to output instructions to the tracking subsystem to instruct the maneuvering subsystem to direct the endoscope to the two surgical tools if the angle between the two surgical tools is less than or if it is greater than the predetermined angle.

According to some embodiments, the preferred volume zone function comprises communicable database comprising n 3D spatial positions; n is an integer greater than or equals to 2; the n 3D spatial positions provides the preferred volume zone; the preferred volume zone function is configured to output instructions to the tracking subsystem to instruct the maneuvering system to direct the endoscope to the preferred volume zone.

According to some embodiments, the field of view function comprises a communicable database comprising n 3D spatial positions; n is an integer greater than or equals to 2; the combination of all of the n 3D spatial positions provides a predetermined field of view; the field of view function is configured to output instructions to the tracking subsystem to instruct the maneuvering system to direct the endoscope to at least one 3D spatial position substantially within the n 3D spatial positions so as to maintain a constant field of view.

According to some embodiments, the no fly zone function comprises a communicable database comprising n 3D spatial positions; n is an integer greater than or equals to 2; the n 3D spatial positions define a predetermined volume within the surgical environment; the no fly zone function is configured to output instructions to the tracking subsystem to instruct the maneuvering system to direct the endoscope to at least one 3D spatial position substantially different from all the n 3D spatial positions.

According to some embodiments, the most used tool function comprises a communicable database counting the amount of movement of each surgical tool located within the surgical environment; the most used tool function is configured to output instructions to the tracking subsystem to instruct the maneuvering system to direct the endoscope to constantly position the endoscope to track the movement of the most moved surgical tool.

According to some embodiments, the prediction function g6($t$) is configured to provide data regarding a surgical environment in a time tf>t, wherein t is the present time and tf is the future time. The prediction function g6($t$) can communicate with a database which stores data regarding the environment of the surgery (e.g., the organs in the environment). This data can be used by the prediction function g6($t$) for the prediction of expected or unexpected events or object during the operation. Thus, according to this embodiment, the prediction function comprises a communicable database storing each 3D spatial position of each of surgical tool within the surgical environment, such that each movement of each surgical tool is stored; the prediction function is configured to (a) to predict the future 3D spatial position of each of the surgical tools; and, (b) to output instructions to the tracking subsystem to instruct the maneuvering system to direct the endoscope to the future 3D spatial position.

According to some embodiments, the past statistical analysis function g7($t$) is configured to provide data regarding the surgical environment or the laparoscopic surgery based on past statistical data stored in a database. The data regarding the surgical environment can be for example: data regarding prohibited areas, data regarding allowed areas, data regarding the region of interest. Thus, according to this embodiment, the past statistical analysis function comprises a communicable database storing each 3D spatial position of each of surgical tool within the surgical environment, such that each movement of each surgical tool is stored; the past statistical analysis function is configured to (a) statistical analyze the 3D spatial positions of each of the surgical tools in the past; and, (b) to predict the future 3D spatial position of each of the surgical tools; and, (c) to output instructions to the tracking subsystem to instruct the maneuvering system to direct the endoscope to the future 3D spatial position. Thus, according to the past statistical analysis function g7($t$), the past movements of each tool are analyzed and according to this analysis a future prediction of the tool's next move is provided.

According to some embodiments, the tagged tool function g15($t$) comprises means configured to tag at least one surgical tool within the surgical environment and to output instructions to the tracking subsystem to instruct the maneuvering subsystem to constantly direct the endoscope to the tagged surgical tool. Thus, according to the tagged tool function the endoscope constantly tracks the preferred (i.e., tagged) tool, such that the field of view, as seen from the endoscope, is constantly maintained on said preferred (tagged) tool. It should be noted that the user can define in said tagged tool function to constantly tack the tip of said preferred (tagged) tool or alternatively, the user can define in said tagged tool function to constantly track the body or any location on the preferred (tagged) tool.

According to some embodiments, the means are configured to constantly tag the at least one of surgical tool within the surgical environment.

According to some embodiments, the system further comprises means configured to re-tag the at least one of the surgical tools until a desired tool is selected.

According to some embodiments, the system further comprises means configured to toggle the surgical tools. According to some embodiments, the toggling is performed manually or automatically.

According to some embodiments, the preferred tool function g16($t$) comprises a communicable database. The database stores a preferred tool; and the preferred tool function is configured to output instructions to the tracking subsystem to instruct the maneuvering subsystem to direct the endoscope to the preferred tool, such that said endoscope constantly tracks said preferred tool.

Thus, according to the preferred tool function the endoscope constantly tracks the preferred tool, such that the field of view, as seen from the endoscope, is constantly maintained on said preferred tool. It should be noted that the user can define in said preferred tool function to constantly tack the tip of said preferred tool or alternatively, the user can define in said preferred tool function to constantly track the body or any location on the preferred tool.

According to some embodiments, the change of speed function g17($t$) comprises a communicable database. The database comprises n 3D spatial positions; n is an integer greater than or equal to 2; the n 3D spatial positions define a predetermined volume within the surgical environment; the change of speed function is configured to determine speed of at least one surgical tool based on a distance between the predetermined volume and at least one location on a surgical tool. For any given time t, the system determines at least two distances, a first distance, X, from at least one predetermined location on a surgical tool to at least one predetermined location associated with the surgical environment, and a second distance, Y, from at least one second predetermined location on the surgical tool to at least one of the n 3D spatial positions. The two predetermined locations on the surgical tool can be the same location. The predetermined locations on the surgical tool can be the tip of the surgical tool, near the tip of the surgical tool, a functional location on a surgical tool such as a location on a blade of a cutter or a location on a movable face of a grasper, or in the body of a surgical tool. The predetermined location in the surgical environment can be any location outside the predetermined volume which is associatable with the surgical tool. Typically, the predetermined location is the point of entry of the surgical tool into the surgical environment or the pivot point of the surgical tool.

For any given time t, the velocity at which the surgical tool is moved is calculated from $$V\text{actual} = f(X,Y) * V\text{predetermined}$$

where Vpredetermined is a predetermined velocity and f(X,Y) is a function of the distances X and Y. Preferably, the function f(X, Y) is selected such that the speed of approach of the surgical tool decreases as the surgical tool approaches the predetermined volume.

According to some embodiments of the present invention, the velocity (speed and direction) varies as a function of the 3D distances X3D and Y3D.

According to some embodiments, the go-to function $g17(t)$ comprises a communicable database; the communicable database is configured to receive an input comprising n 3D spatial positions; n is an integer greater than or equal to 1 such that allowed movement is either a movement in which an endoscope is re-directed to focus on at least one of the n 3D spatial positions, a movement in which a tagged tool is re-directed to position at least a portion of the tagged tool on at least one of said n 3D spatial positions or a movement in which a surgical tool is re-directed to position at least a portion of the tagged tool on at least one of the n 3D spatial positions.

According to some embodiments of the present invention, the weighting functions $\alpha i(t)$ are time-varying functions (or constants), the value of which is determined by the operator or the output of the instructing functions $gi(t)$. For example, if a specific function $gi(t)$ detected an important event or object, its weighting functions $\alpha i(t)$ can be adjusted in order to elevate the chances that the maneuvering function $f(t)$ will instruct the maneuvering subsystem to move the endoscope towards this important event or object.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

One embodiment of such a rule-based system will comprise the following set of commands:
Detection (denoted by Gd):
Gd1 Tool location detection function
Gd2 Organ (e.g. Liver) detection function
Gd3 Movement (vector) calculation and estimation function
Gd4 Collision probability detection function
Tool Instructions (denoted Gt):
Gt1 Move according to manual command
Gt2 Stop movement
The scenario—manual move command by the surgeon:
Locations $Gd1(t)$ and $Gd2(t)$ are calculated in real time at each time step (from an image or location marker).
Tool movement vector $Gd3(t)$ is calculated from $Gd1(t)$ as the difference between the current location and at least one previous location (probably also taking into account previous movement vectors).
The probability of collision—$Gd4(t)$—is calculated, for example, from the difference between location Gd1 and location Gd2 (the smaller the distance, the closer the proximity and the higher the probability of collision), from movement vector $Gd3(t)$ indicating a collision, etc.
Tool Instructions Gt1 Weight function $\alpha 1(t)=1$ If $Gt1(t)<a$ predetermined threshold and 0 otherwise
Tool Instructions Gt2 Weight function $\alpha 2(t)=1$ If $Gt2(t)>a$ predetermined threshold and 0 otherwise Tool Instructions=$\alpha 1(t)*Gt1+\alpha 2(t)*Gt2(t)$;

In reference to FIG. 3, which shows, in a non-limiting manner, an embodiment of a tracking system and collision avoidance system. The system tracks a tool (310) and the liver (320), in order to determine whether a collision between the tool (310) and the liver (320) is possible within the next time step. FIGS. 3a and 3b show how the behavior of the system depends on the distance (330) between the tool (310) and the liver (320), while FIGS. 3c and 3d show how movement of the tool (310) affects the behavior. In FIG. 3a, the distance (330) between the tool (310) and the liver (320) is large enough that a collision is not possible in that time step. Since no collision is possible, no movement of the tool is commanded. In FIG. 3b, the distance (330) between the tool (310) and the liver (320) is small enough that a collision is likely. In the embodiment illustrated, a movement (340) is commanded to move the tool (310) away from the liver (320). In other embodiments, the system prevents movement 350, but does not command movement (340); in such embodiments, the tool (310) will remain close to the liver (320). In yet other embodiments, the system warns/signals the operator that the move is restricted, but does not restrict movement 350 or command movement (340) away from the liver. Such a warning/signaling can be visual or aural, using any of the methods known in the art.

Figure 3A:
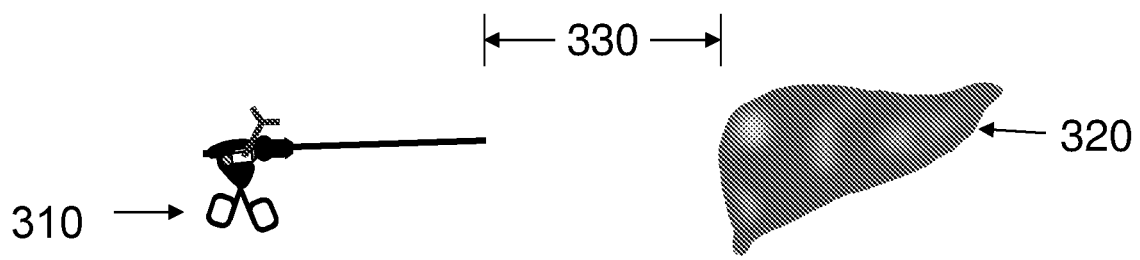
FIG. 3a-d schematically illustrates operation of an embodiment of a tracking system with collision avoidance system.
Figure 3B:
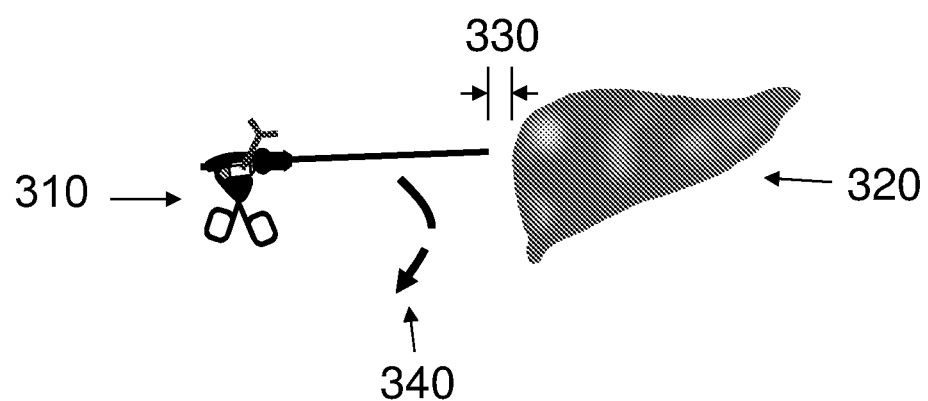
Figure 3C:
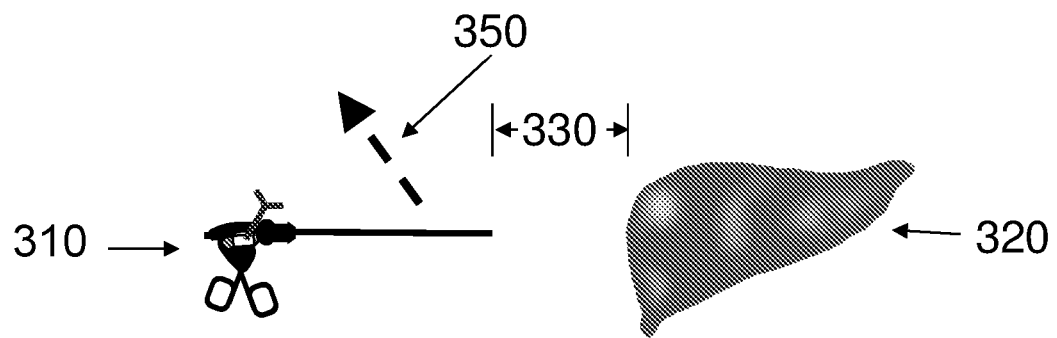
Figure 3D:
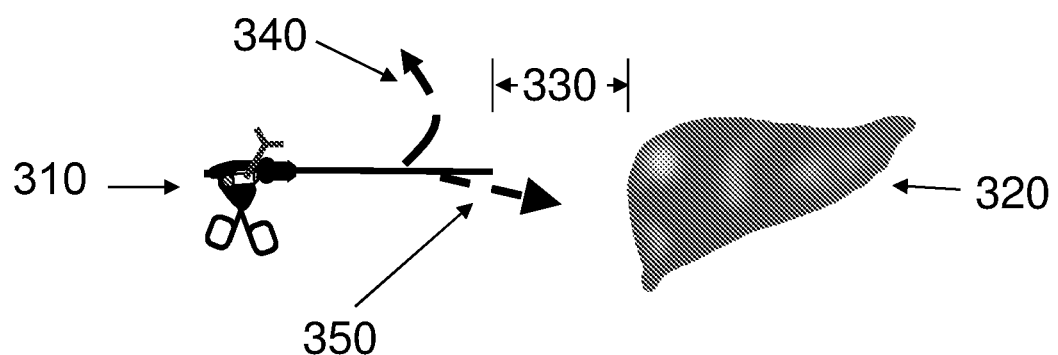

FIGS. 3c and 3d illustrate schematically the effect of the movement of tool (310) on the collision avoidance system. In FIGS. 3c and 3d, the tool (310) is close enough to the liver (320) that a collision between the two is possible. If the system tracked only the positions of the tool (310) and the liver (320), then motion of the tool (310) away from the liver (320) would be commanded. FIG. 3c illustrates the effect of a movement 350 that would increase the distance between tool (310) and liver (320). Since the movement 350 is away from liver (320), no collision is possible in this time step and no movement of the tool (310) is commanded.

In FIG. 3d, tool (310) is the same distance from liver (320) as in FIG. 3c. However, in FIG. 3d, the movement 350 of the tool (310) is toward the liver (320), making a collision between tool (310) and liver (320) possible. In some embodiments, a movement (340) is commanded to move the tool (310) away from the liver (320). In other embodiments, the system prevents movement 350, but does not command movement (340); in this embodiment the tool (310) will remain close to the liver (320). In yet other embodiments, the system warns the operator that move is restricted, but does not restrict movement 350 or command movement (340) away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver.

Example 2—Tracking System with Soft Control—Fast Movement when Nothing is Nearby, Slow Movement when Something is Close One embodiment of such rule-based system comprises the following set of commands:
Detection (denoted by Gd):
Main Tool location detection function (denoted by GdM);
Gd-tool1-K—Tool location detection function;
Gd-organ2-L—Organ (e.g. Liver) detection function;

Gd3 Main Tool Movement (vector) calculation and estimation function;

Gd4 Proximity probability detection function;

Tool Instructions (denoted Gt):

Gt1 Movement vector (direction and speed) according to manual command

The scenario—manual move command by the surgeon:

Locations GdM(t), Gd-tool1-K(t) and Gd-organ2-L(t) are calculated in real time at each time step (from image or location marker).

Main Tool Movement Vector Gd3(*t*) is calculated per GdM (t) as the difference between the current location and at least one previous location (probably also taking into account previous movement vectors)

The proximity of the main tool to other tools—Gd4(*t*)—is calculated, for example, as the smallest of the differences between the main tool location and the other tools' locations.

Tool Instructions Gt1 Weight function α1(*t*) is proportional to tool proximity function Gd4(*t*), the closer the tool the slower the movement so that, for example $$\alpha 2(t)=Gd4/\text{maximum}(Gd4)$$

or $$\alpha 2(t)=\log(Gd4/\text{maximum}(Gd4))$$

where maximum(Gd4) is the maximum distance which is likely to result in a collision given the distances, the speed of the tool and the movement vector.

$$\text{Tool Instructions}=\alpha 1(t)*Gt1$$

Example 3—Tracking System with No-Fly Rule/Function

In reference to FIG. 4, which shows, in a non-limiting manner, an embodiment of a tracking system with no-fly rule. The system tracks a tool (310) with respect to a no-fly zone (460), in order to determine whether the tool will enter the no-fly zone (460) within the next time step. In this example, the no-fly zone 460 surrounds the liver.

Figure 4A:
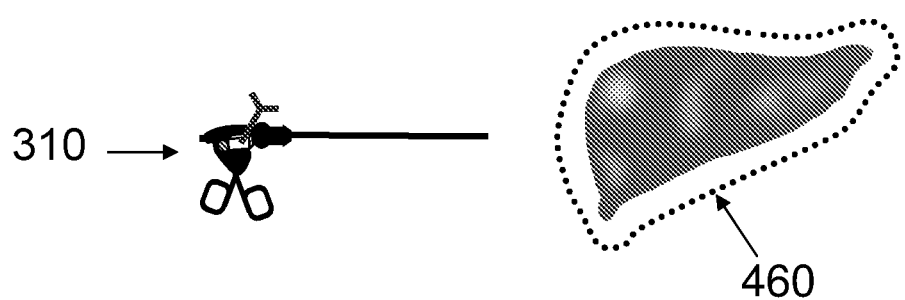
FIG. 4a-d schematically illustrates operation of an embodiment of a tracking system with no fly zone rule/function.
Figure 4B:
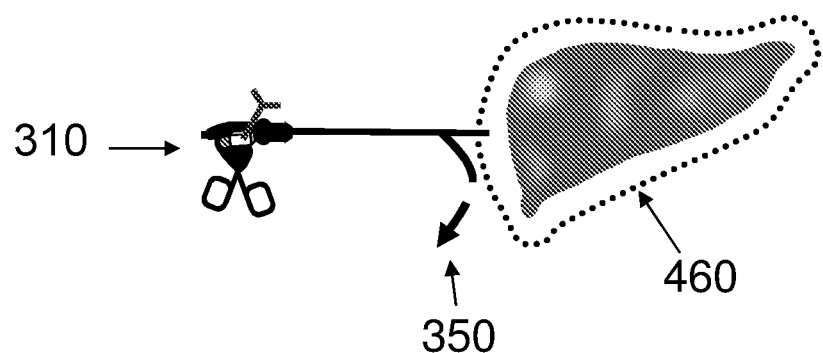
Figure 4C:
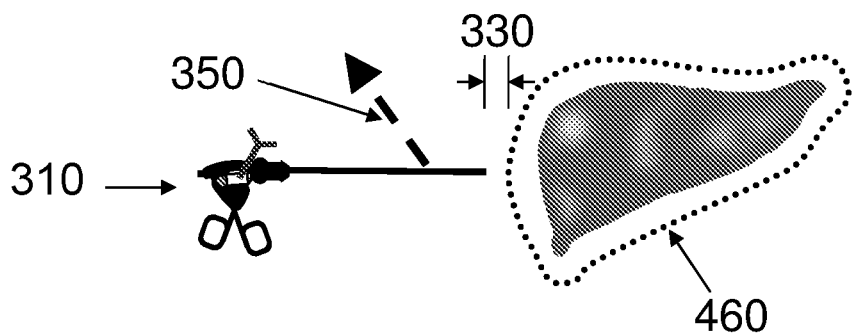
Figure 4D:
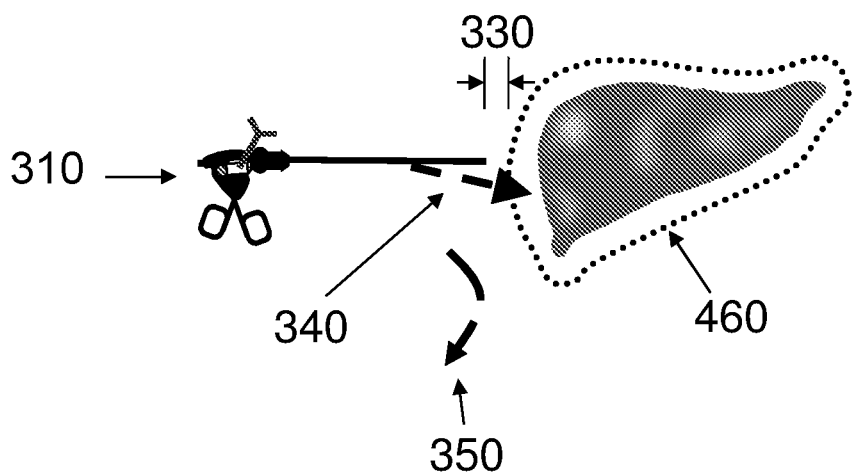

FIGS. 4*a* and 4*b* show how the behavior of the system depends on the location of the tool tip with respect to the no-fly zone, while FIGS. 4*c* and 4*d* show how movement of the tool affects the behavior.

In FIG. 4*a*, the tool (310) is outside the no-fly zone rule/function 460 and no movement of the tool is commanded. In FIG. 4*b*, the tool (310) is inside the no-fly zone 460.

The no-fly zone rule/function performs as follows:

In the embodiment illustrated, a movement 350 is commanded to move the tool (310) away from the no-fly zone 460. In other embodiments, the system prevents movement further into the no-fly zone (refers as movement (340), see FIG. 4*c*), but does not command movement (340); in such embodiments, the tool (310) will remain close to the no-fly zone 460.

In yet other embodiments, the system warns/signals the operator that the move is restricted, but does not restrict movement further into the no-fly zone or command movement (340) away from the no-fly zone 460. Such a warning/signaling can be visual or aural, using any of the methods known in the art.

FIGS. 4*c* and 4*d* illustrate schematically the effect of the tool's movement on operation of the no-fly zone rule/function. In FIGS. 4*c* and 4*d*, the tool (310) is close enough to the no-fly zone 460 (the distance (330) is small enough) that it is possible for the tool to enter the no-fly zone during the next time step. FIG. 4*c* illustrates the effect of a movement 340 that would increase the distance between tool (310) and no-fly zone 460. Since the movement 340 is away from no-fly zone 460, no collision is possible in this time step and no movement of the tool (310) is commanded.

In FIG. 4*d*, tool (310) is the same distance from no-fly zone 460 as in FIG. 4*c*. However, in FIG. 4*d*, the movement 340 of the tool is toward no-fly zone 460, making it possible for tool (310) to enter no-fly zone 460. In the embodiment illustrated, a movement 350 is commanded to move the tool (310) away from the no-fly zone 460. In other embodiments, the system prevents movement 340, but does not command movement 350; in such embodiments, the tool (310) will remain close to the no-fly zone 460. In yet other embodiments, the system warns/signals the operator that the move is restricted, but does not restrict movement 340 or command movement 350 away from the no-fly zone rule/function 460. Such a warning/signaling can be visual or aural, using any of the methods known in the art.

Example 4—Tracking System with Preferred Volume Zone Rule/Function

In reference to FIG. 5, which shows, in a non-limiting manner, an embodiment of a tracking system with a preferred volume zone function/rule.

The system tracks a tool (310) with respect to a preferred volume zone (570), in order to determine whether the tool will leave the preferred volume (570) within the next time step.

Figure 5A:
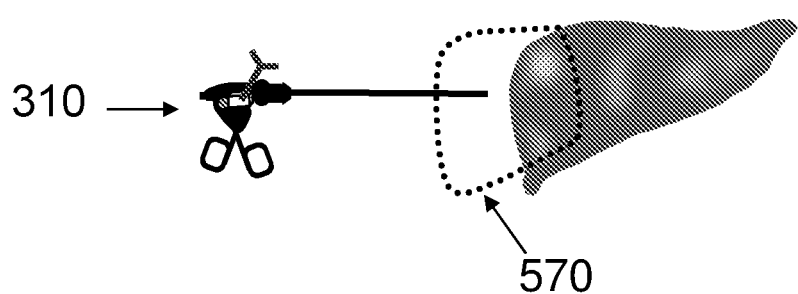
FIG. 5a-d schematically illustrates operation of an embodiment of a tracking system with preferred volume zone rule/function.
Figure 5B:
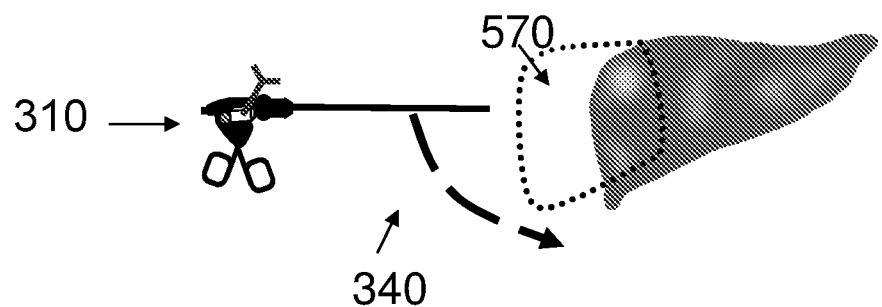

In this example, the preferred volume zone 570 extends over the right lobe of the liver. FIGS. 5*a* and 5*b* show how the behavior of the system depends on the location of the tool tip with respect to the preferred volume zone 570, while FIGS. 5*c* and 5*d* show how movement of the tool affects the behavior (i.e., the preferred volume zone rule/function).

In FIG. 5*a*, the tool (310) is inside the preferred volume zone 570 and no movement of the tool is commanded. In FIG. 5*b*, the tool (310) is outside the preferred volume zone 570.

In the embodiment illustrated, a movement 340 is commanded to move the tool (310) away from the preferred volume zone 570. In other embodiments, the system prevents movement 340; in such embodiments, the tool (310) will remain close to the preferred volume zone 570. In yet other embodiments, the system warns/signals the operator that the move 340 is restricted. Such a warning/signaling can be visual or aural, using any of the methods known in the art.

Figure 5C:
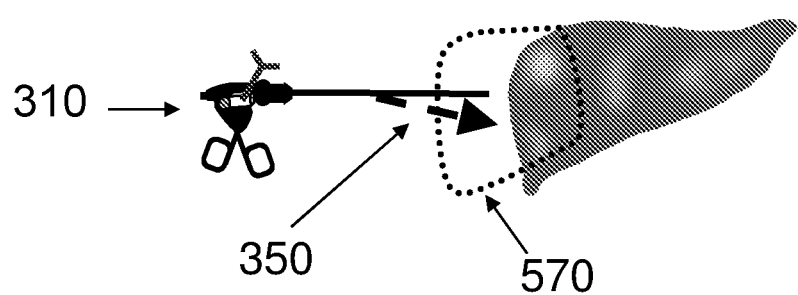
Figure 5D:
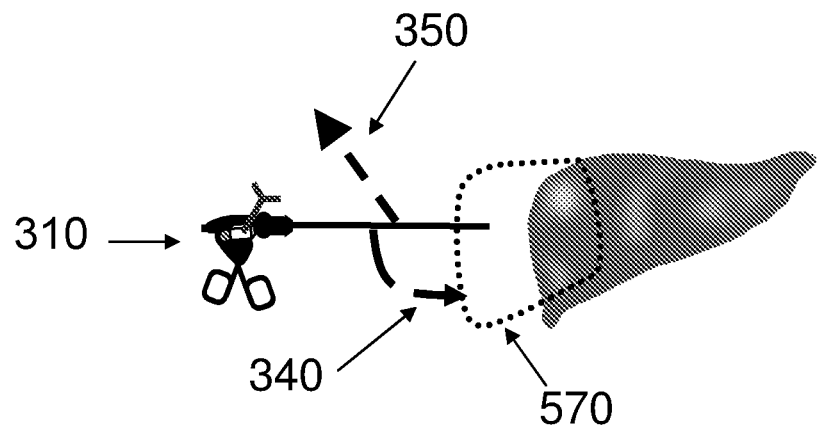

FIGS. 5*c* and 5*d* illustrate schematically the effect of the tool's movement on operation of the preferred volume rule/function. In FIGS. 5*c* and 5*d*, the tool (310) is close enough to the edge of preferred volume zone 570 that it is possible for the tool to leave the preferred volume zone during the next time step.

FIG. 5*c* illustrates the effect of a movement 350 that would take the tool (310) deeper into preferred volume zone 570. Since the movement 350 is into preferred volume 570, said movement is an allowed movement.

In FIG. 5*d*, the movement 350 of the tool is out of the preferred volume 570, making it possible for tool (310) to leave preferred volume 570.

According to one embodiment illustrated, a movement 340 is commanded to move the tool (310) into the preferred volume zone 570. In other embodiments, the system prevents movement 350, but does not command movement

340; in such embodiments, the tool (310) will remain close to the preferred volume zone 570. In yet other embodiments, the system warns/signals the operator that the move is restricted, but does not restrict movement 350 or command movement 340 away from the preferred volume zone 570. Such a warning/signaling can be visual or aural, using any of the methods known in the art.

Example 5—Organ/Tool Detection Function

Figure 6:
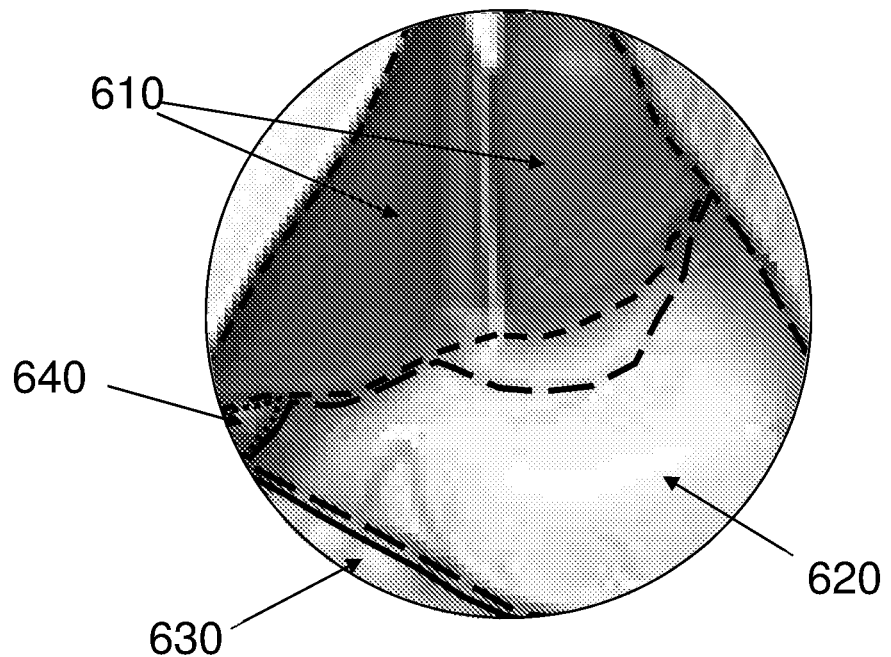
FIG. 6 schematically illustrates operation of an embodiment of the organ detection function/rule.

In reference to FIG. 6, which shows, in a non-limiting manner, an embodiment of an organ detection system (however, it should be noted that the same is provided for detection of tools, instead of organs).

For each organ, the 3D spatial positions of the organs stored in a database. In FIG. 6, the perimeter of each organ is marked, to indicate the edge of the volume of 3D spatial locations stored in the database.

In FIG. 6, the liver 610 is labeled with a dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 7:
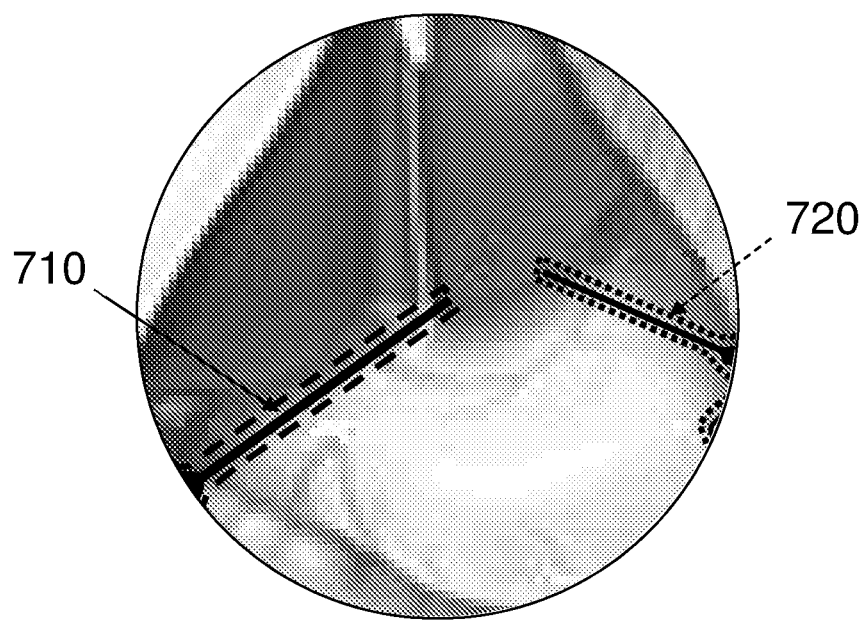
FIG. 7 schematically illustrates operation of an embodiment of the tool detection function/rule.

In reference to FIG. 7, which shows, in a non-limiting manner, an embodiment of a tool detection function. For each tool, the 3D spatial positions of the tools stored in a database. In FIG. 7, the perimeter of each tool is marked, to indicate the edge of the volume of 3D spatial locations stored in the database. In FIG. 7, the left tool is labeled with a dashed line while the right tool is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 8A:
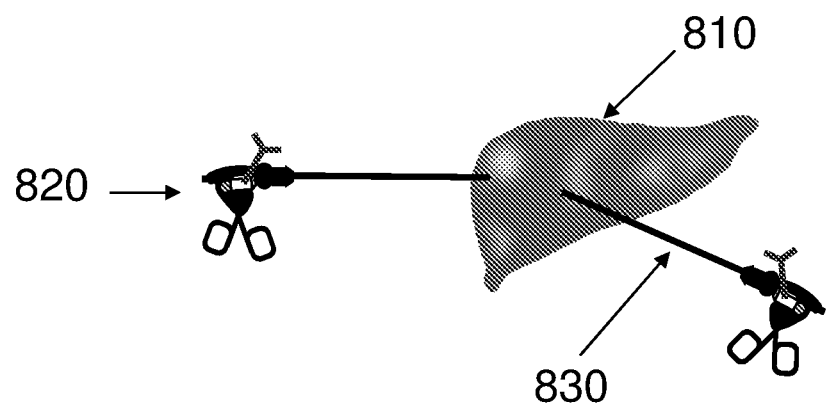
FIG. 8a-b schematically illustrates operation of an embodiment of the movement detection function/rule.
Figure 8B:
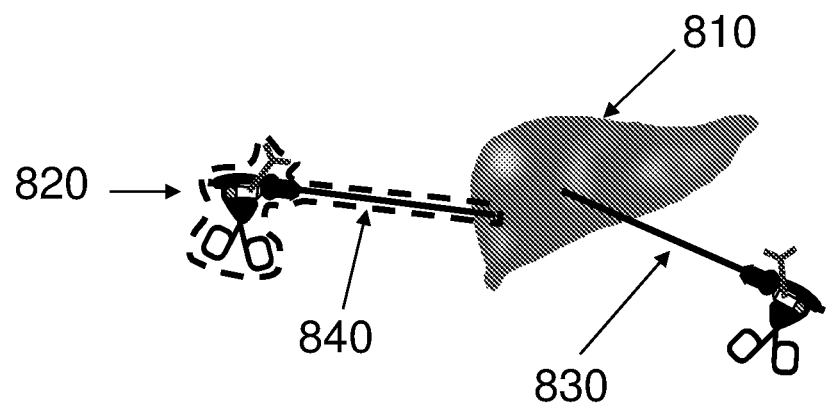

In reference to FIG. 8, which shows, in a non-limiting manner, an embodiment of a movement detection function/rule. FIG. 8a schematically illustrates a liver 810, a left tool 820 and a right tool 830 at a time t. FIG. 8b schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 8b by a dashed line around left tool 820.

Example 8—Prediction Function

In reference to FIG. 9, which shows, in a non-limiting manner, an embodiment of the above discussed prediction function.

Figure 9A:
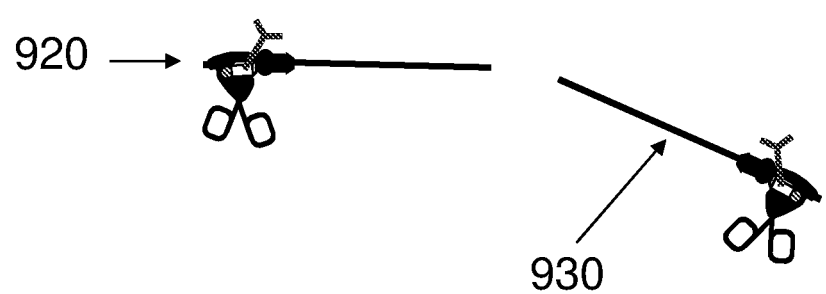
FIG. 9a-d schematically illustrates operation of an embodiment of the prediction function/rule.

FIG. 9a shows a left tool 920 and a right tool 930 at a time t.

Figure 9B:
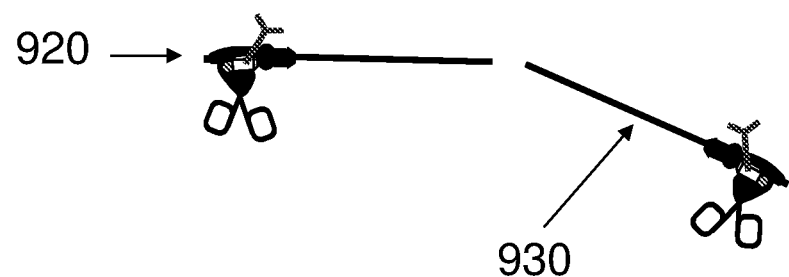
Figure 9C:
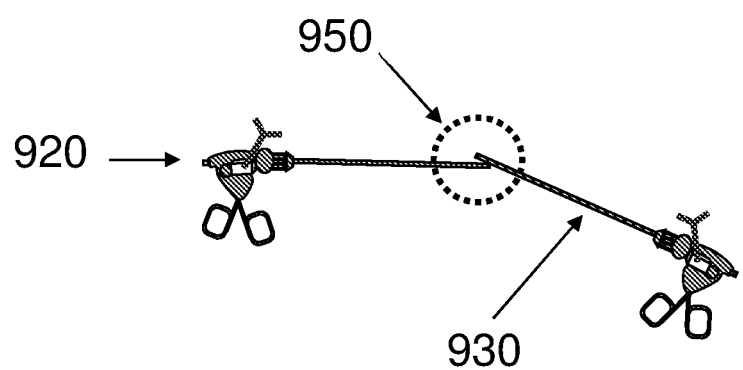
Figure 9D:
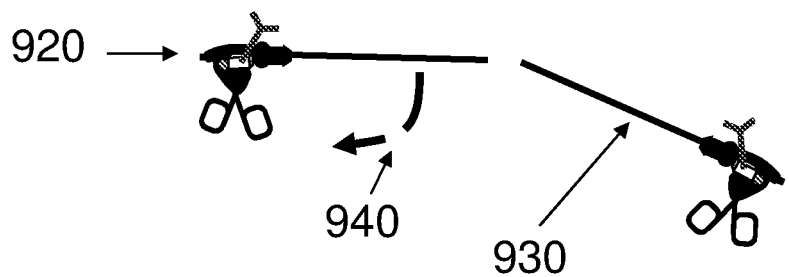

FIG. 9b shows the same tools at a later time t+Δt, where Δt is a small time interval. Left tool 920 is moving to the right and downward, while right tool 930 is moving to the left and upward. If the motion continues (shown by the dashed line in FIG. 9c), then by the end of the next time interval, in other words, at some time between time t+Δt and time t+2Δt, the tools will collide, as shown by tool tips within the dotted circle 950 in FIG. 9c.

In this embodiment, the system automatically prevents predicted collisions and, in this example, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 10:
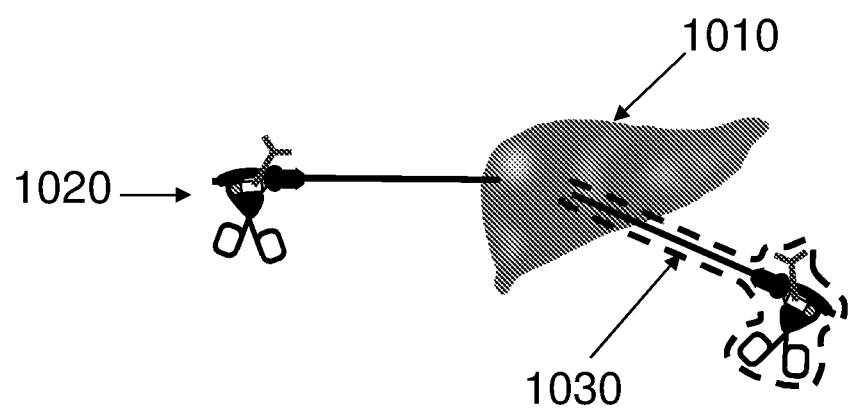
FIG. 10 schematically illustrates operation of an embodiment of the right tool function/rule.

In reference to FIG. 10, which shows, in a non-limiting manner, an embodiment of a right tool function. FIG. 10 schematically illustrates a liver 1010, a left tool 1020 and a right tool 1030. The right tool, illustrated schematically by the dashed line 1040, is labeled and its 3D spatial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

In reference to FIG. 11, which shows, in a non-limiting manner, an embodiment of a field of view function/rule.

Figure 11A:
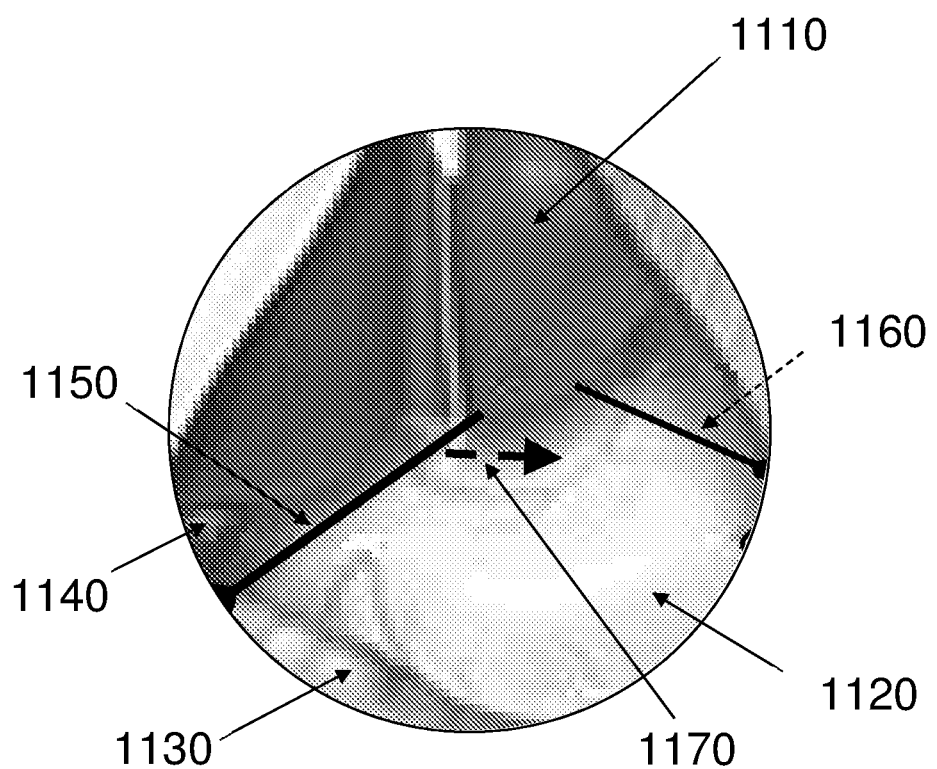
FIG. 11a-b schematically illustrates operation of an embodiment of the field of view function/rule.

FIG. 11a schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

Figure 11B:
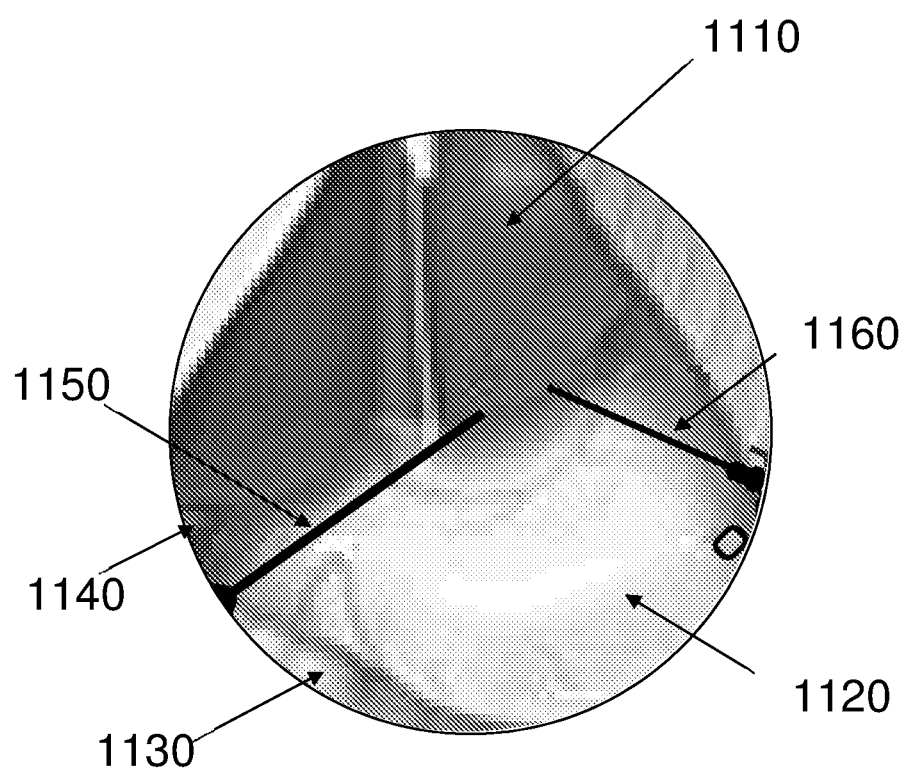

FIG. 11b shows the field of view at time t+Δt. The field of view has moved to the right so that the tip of left tool 1150 is still nearly at the center of the field of view. It can be seen that much less of gall bladder 1140 is visible, while more of right tool 1160 has entered the field of view.

The field of view function/rule can be set to follow a selected tool, as in this example or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 12:
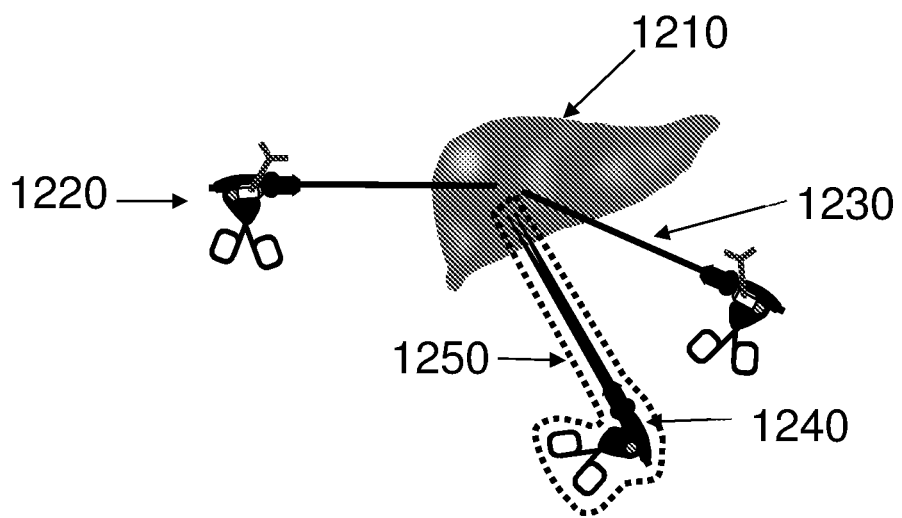
FIG. 12 schematically illustrates operation of an embodiment of the tagged tool function/rule.

In reference to FIG. 12, which shows, in a non-limiting manner, an embodiment of a tagged tool function/rule.

FIG. 12 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spatial location of tool 1240 is constantly stored in a database and this spatial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track said tagged tool 1250 and so on.

It should be noted that in the preferred tool rule, the system tags one of the tools and performs as in the tagged tool rule/function.

Example 12—Proximity Function/Rule

In reference to FIG. 13, which shows, in a non-limiting manner, an embodiment of a proximity function/rule.

Figure 13A:
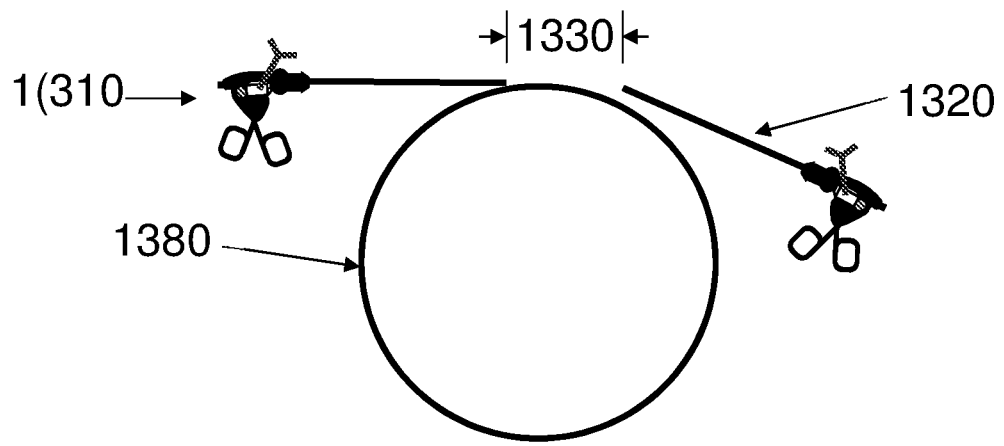
FIG. 13a-c schematically illustrates operation of an embodiment of the proximity function/rule.

FIG. 13a schematically illustrates two tools (1310 and 1320) separated by a distance 1330 which is greater than a predefined proximity distance. Since tool 1310 is not within proximity of tool 1320, the field of view (1380) does not move.

Figure 13B:
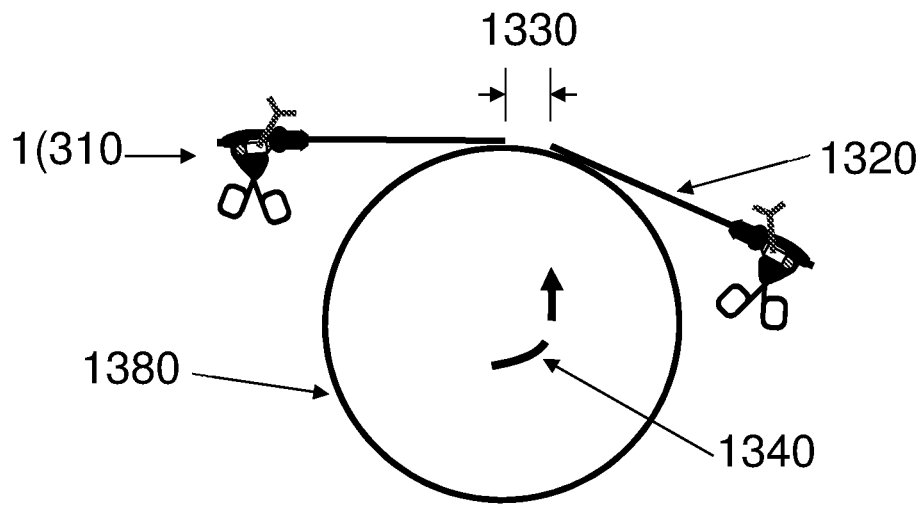

FIG. 13b schematically illustrates two tools (1310 and 1320) separated by a distance 1330 which is less than a predefined proximity distance.

Figure 13C:
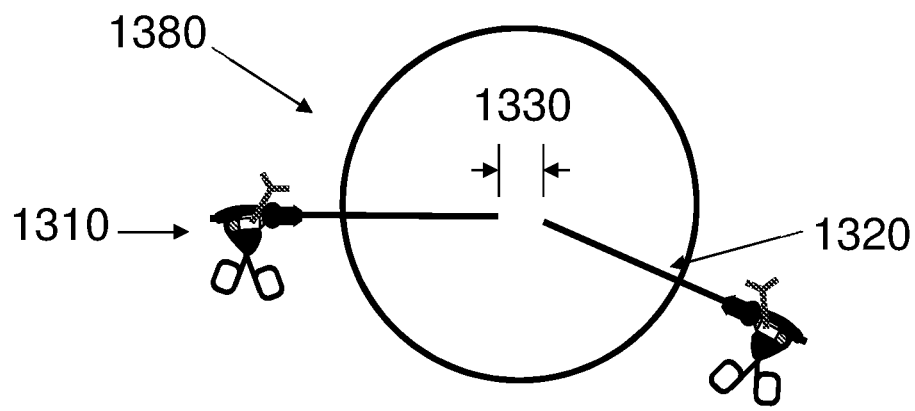

Since tool 1310 is within proximity of tool 1320, the field of view 1380 moves upward, illustrated schematically by arrow 1340, until the tips of tool 1(310) and tool 1320 are in the center of field of view 1380 (FIG. 13c).

Alternatively the once the distance (1330) between the two tool (1320) and (1310) is smaller than a predetermined distance, the system alerts the user of said proximity (which might lead to a collision between the two tools). Alternatively, the system moves one of the tools away from the other one.

Example 13—Operator Input Function/Rule

In reference to FIG. 14, which shows, in a non-limiting manner, an embodiment of an operator input function/rule. According to this embodiment, input is received from the operator.

In the following example, the input received from the operator is which tool to track.

Figure 14A:
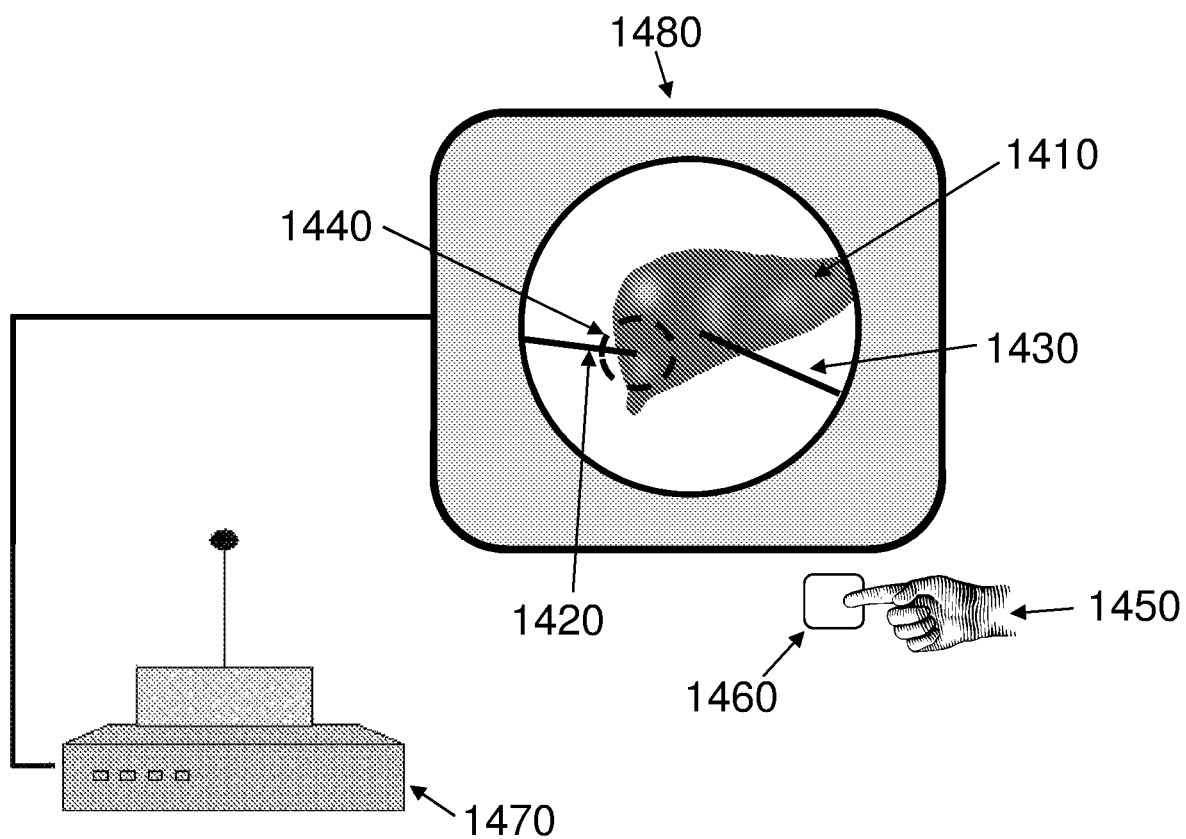
FIG. 14a-b schematically illustrates operation of an embodiment of the operator input function/rule.

FIG. 14a schematically illustrates an endoscope with field of view 1480 showing a liver 1410 and two tools 1420 and 1430. A wireless transmitter 1460 is enabled to transmit coded instructions through receiver 1470. Operator 1450 first selects the tip of the left tool as the region of interest, causing the system to tag (1440) the tip of the left tool.

Figure 14B:
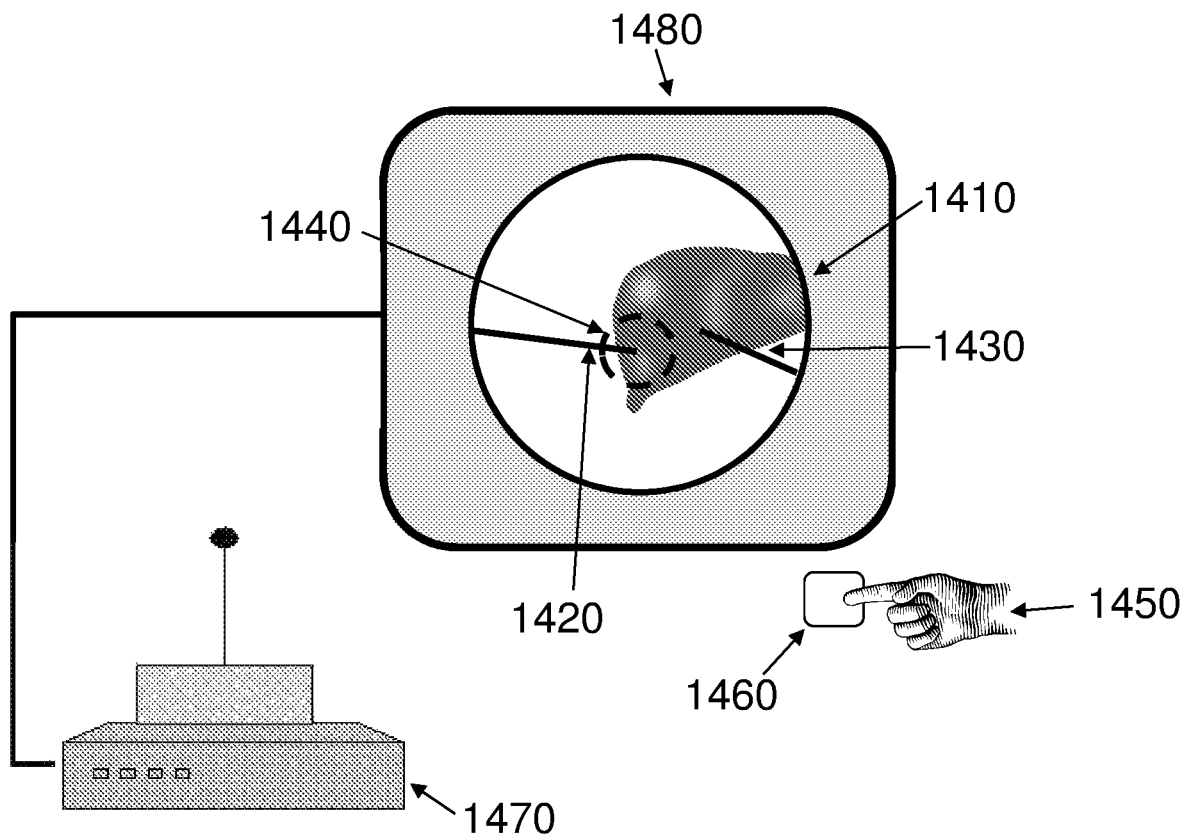

As illustrated in FIG. 14b, the system then directs and modifies the spatial position of the endoscope so that the tagged tool tip 1440 is in the center of the field of view 1480.

Another example of the operator input function/rule is the following:

If a tool has been moved closely to an organ in the surgical environment, according to the proximity rule or the collision prevention rule, the system will, according to one embodiment, prevent the movement of the surgical tool.

According to one embodiment of the present invention, once the surgical tool has been stopped, any movement of said tool in the direction is interpreted as input from the operator to continue the movement of said surgical tool in said direction.

Thus, according to this embodiment, the operator input function/rule receives input from the operator (i.e., physician) to continue the move of said surgical tool (even though it is "against" the collision prevention rule). Said input is simply in the form of the continued movement of the surgical tool (after the alert of the system or after the movement prevention by the system).

Example 14—Constant Field of View Rule/Function

In reference to FIGS. 15a-D, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0.

Typically, angled endoscope tip lenses have an angle of 30° or 45°. This tip lens angle affects the image seen during zooming. FIG. 15 illustrates, in an out-of-scale manner, for a conventional system, the effect of zooming in the field of view in an endoscope with tip lens set straight in the end (FIGS. 15a and 15b) vs. the effect of zooming in the field of view in an endoscope with angled tip lens (FIGS. 15c and 15d).

Figure 15A:
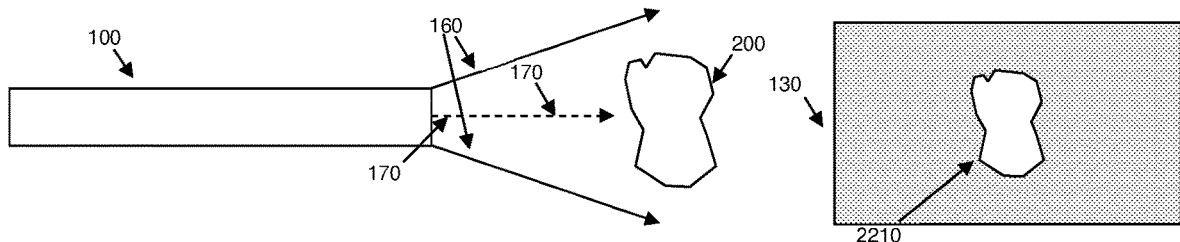
FIGS. 15a-d schematically illustrate an embodiment of a tracking system with a constant field of view rule/function.
Figure 15B:
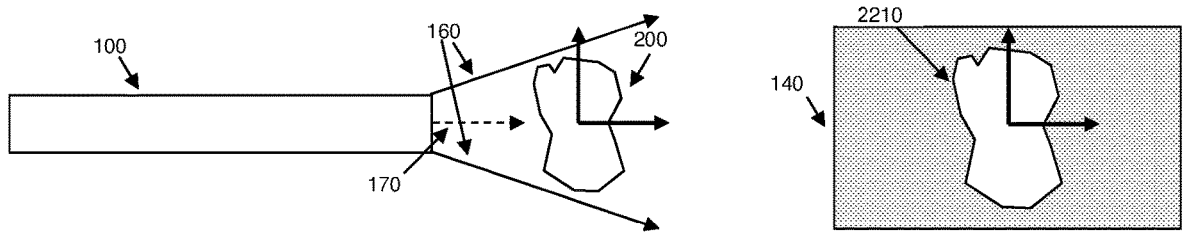
Figure 15C:
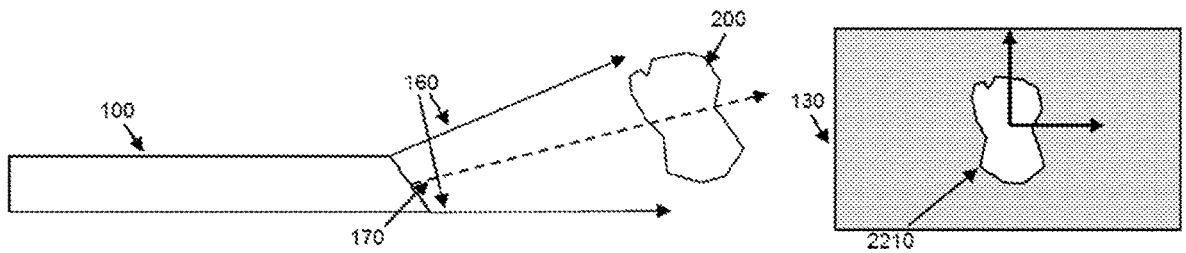
Figure 15D:
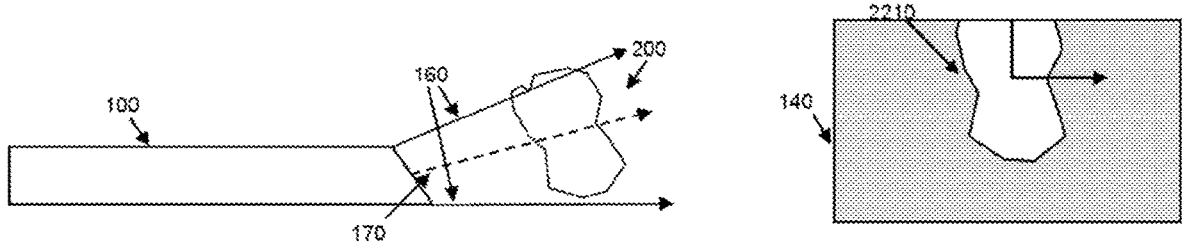

FIGS. 15a and 15c illustrate the endoscope (100), the object it is viewing (200) and the image seen by the endoscope camera (130) before the zoom. The solid arrows (160) show the limits of the FOV and the dashed arrow (170), the center of the field of view (FOV); since the object is in the center of the FOV, an image of the object (2210) is in the center of the camera image (130). FIGS. 3B and 3D illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 15a and 15b), an object (200) in the center of the field of view will be in the center of the field of view (FOV) (and the camera image) (130) both before (FIG. 15a) and after (FIG. 15b) the zoom. However, if the tip lens is set at an angle in the end of the endoscope (FIGS. 15C and 15D), then an object that is in the center of the FOV (and the camera image) before the zoom (FIG. 15C) will not be in the center of the FOV (or the camera image) after the zoom (FIG. 15D)

since the direction of motion of the endoscope is not the direction in which the center of the field of view (170) points.

In an embodiment of the system of the present invention, unlike in conventional systems, the controlling means maintains the center of the field of view (FOV) during zoom independent of the tip lens angle. An advantage of controlling the zoom of the endoscope via a data processing system is that the tip lens angle does not need to be input to the data processing system, obviating a possible source of error.

According to one embodiment of the present invention, the endoscope's movement will be adjusted in order to maintain a constant field of view.

Example 15—Misalignment Rule/Function

According to some embodiments of the present invention, the system can inform the user of any misalignment of the same system.

Misalignment of the system may cause parasitic movement of the endoscope tip, where the endoscope tip does not move exactly in the expected direction. According to one embodiment of the system, the system comprises sensors (e.g., gyroscopes, accelerometers and any combination thereof) that calculate/estimates the position of the pivot point in real time in order to (a) inform the user of misalignment; or (b) calculate the misalignment so that the system can adjust its movement to prevent parasitic movement.

Example 16—Change of Speed Rule/Function

Figure 16:
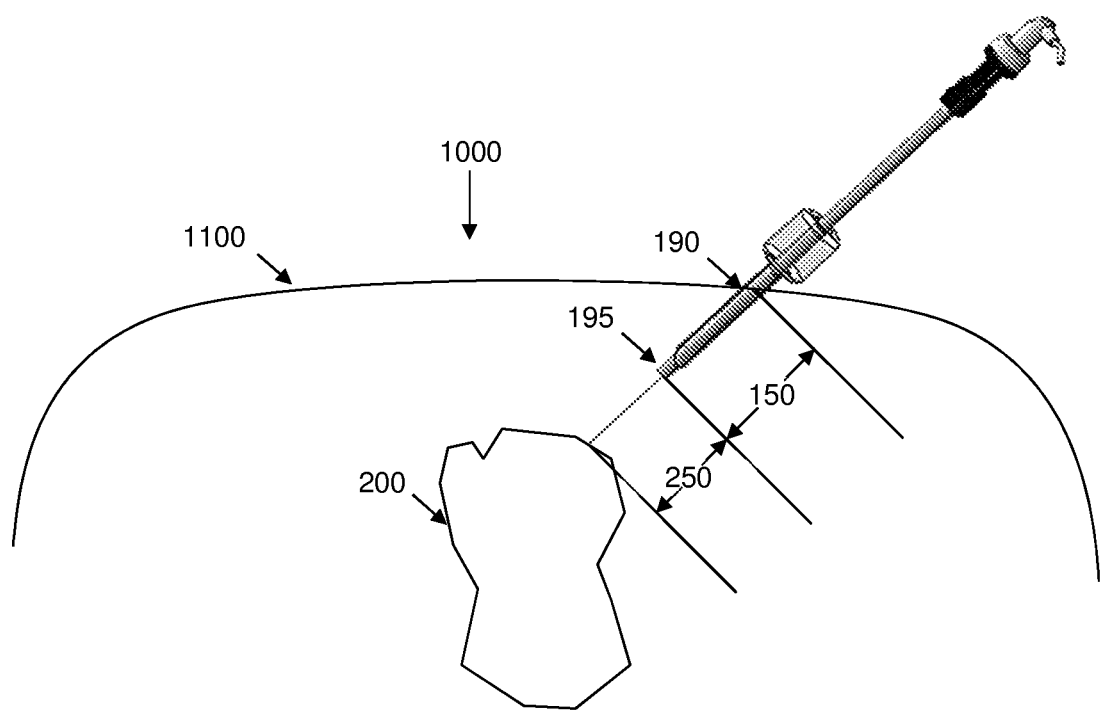
FIG. 16 schematically illustrates an embodiment of a tracking system with a change of speed rule/function.

In reference to FIG. 16, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 7, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object in the center of the scene of view (200). From a predetermined velocity Vp, the actual velocity of the tip of the endoscope at a given time, Vact, is calculated from $$V_{act} \propto \frac{Y}{X} V_p$$

Vact∝YX Vp

Therefore, the closer to the object at the center of the scene of view, the more slowly the endoscope moves, making it possible to use automatic control of even fine adjustments, and reducing the probability that the endoscope will come in contact with tissue or instruments.

In some embodiments of the system, the harder the control unit is pressed, the faster the endoscope tip moves. In these embodiments, the system provides a warning if the speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to some embodiments of the present invention, the velocity (speed and direction) of the endoscope's movement can be adjusted as a function of the distance of the endoscope's tip from the organ\tissue.

Example 17—Go-To Rule/Function

In reference to FIG. 17, which shows, in a non-limiting manner, an embodiment of a tracking system with a go-to rule/function.

In the following example, input is received from an operator of a location and the endoscope is maneuvered to put the location at the center of the FOV.

Figure 17A:
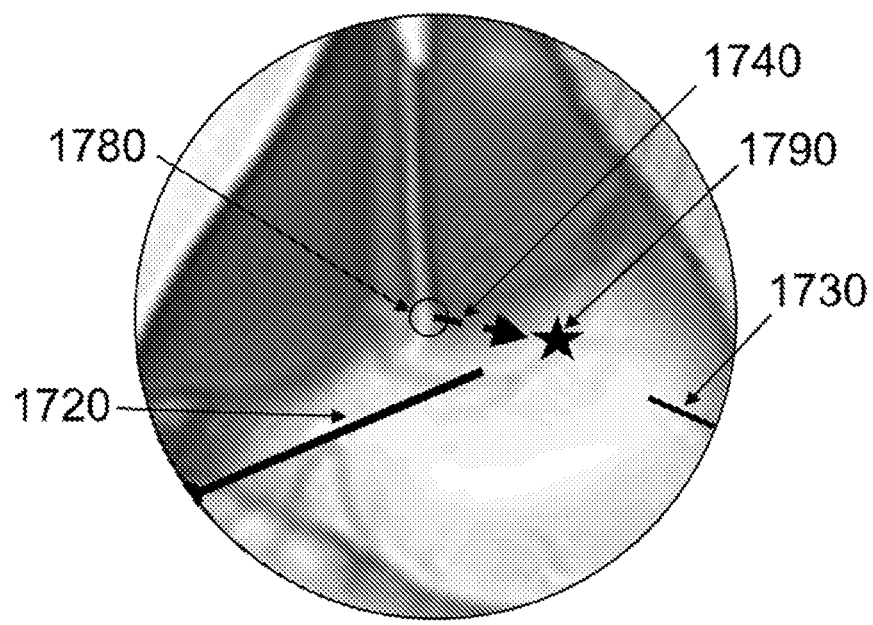
FIGS. 17a-b and 18a-b schematically illustrate an embodiment of a tracking system with a go-to rule/function.

FIG. 17*a* schematically illustrates an endoscope with field of view having a center 1780. Two tools 1720 and 1730 are visible in the FOV. A location 1790 is input to the system. A movement 1740 can be commanded to move the center of the FOV from its present position to the location 1790 which was input.

Figure 17B:
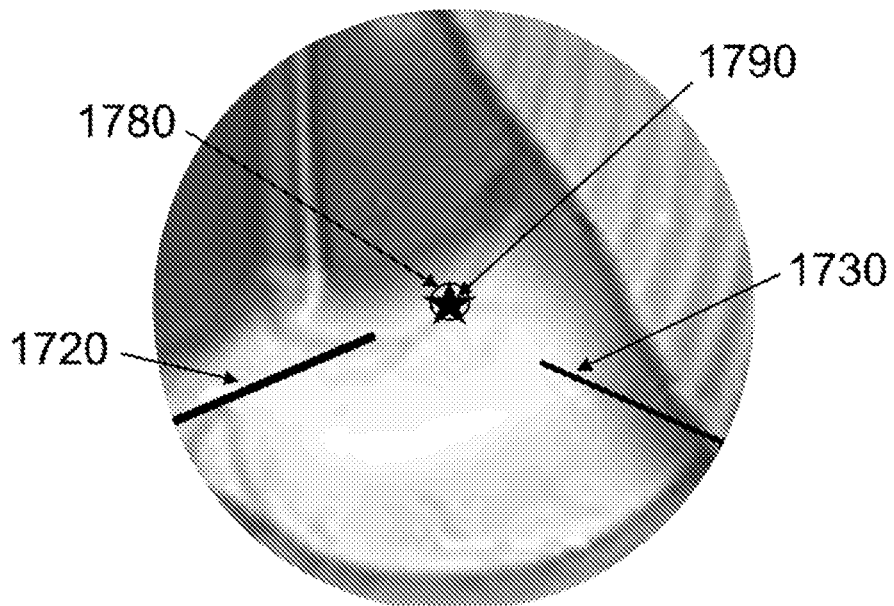

As illustrated in FIG. 17*b*, the system then directs and modifies the spatial position of the endoscope so that the location 1790 is in the center 1780 of the FOV. The tools 1720 and 1730 have not been moved.

Example 18—Go-To Rule/Function

In reference to FIG. 18, which shows, in a non-limiting manner, an embodiment of a tracking system with a go-to rule/function.

In the following example, input is received from an operator of a location and a tagged tool is maneuvered to put the tagged tool at the center of the FOV.

Figure 18A:
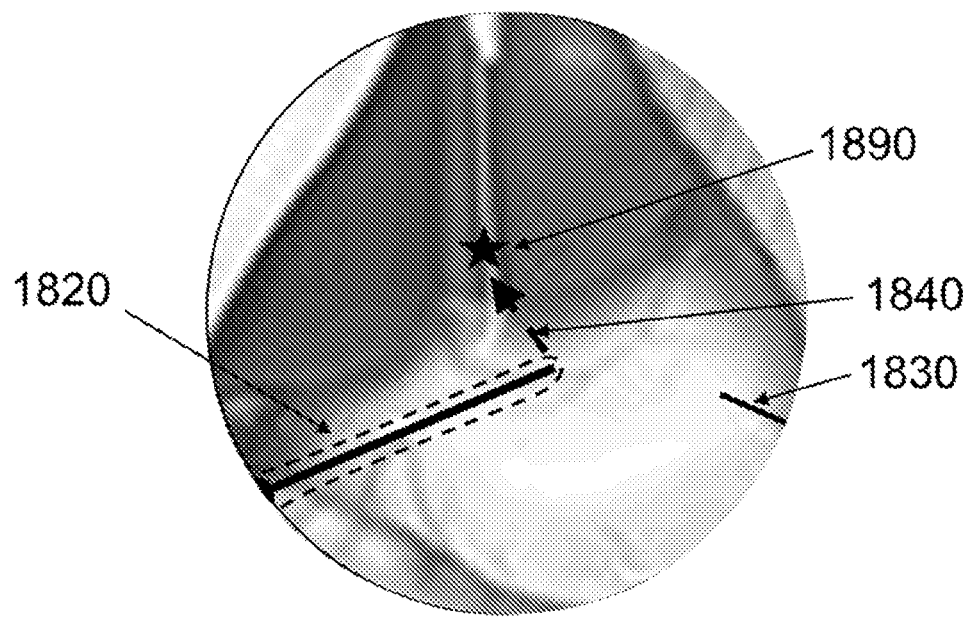

FIG. 18*a* schematically illustrates an FOV of an endoscope. Two tools 1820 and 1830 are visible in the FOV; the dashed line indicated the tagged tool. A location 1890 is input to the system. A movement 1840 can be commanded to move the tagged tool 1820 from its present position to the location 1890 which was input.

Figure 18B:
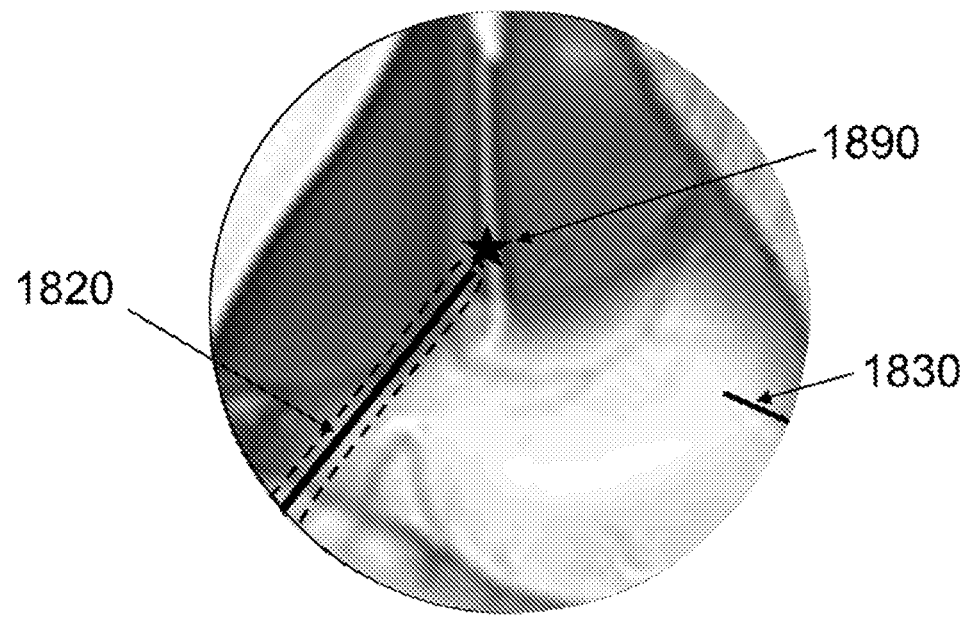
Figure 19:
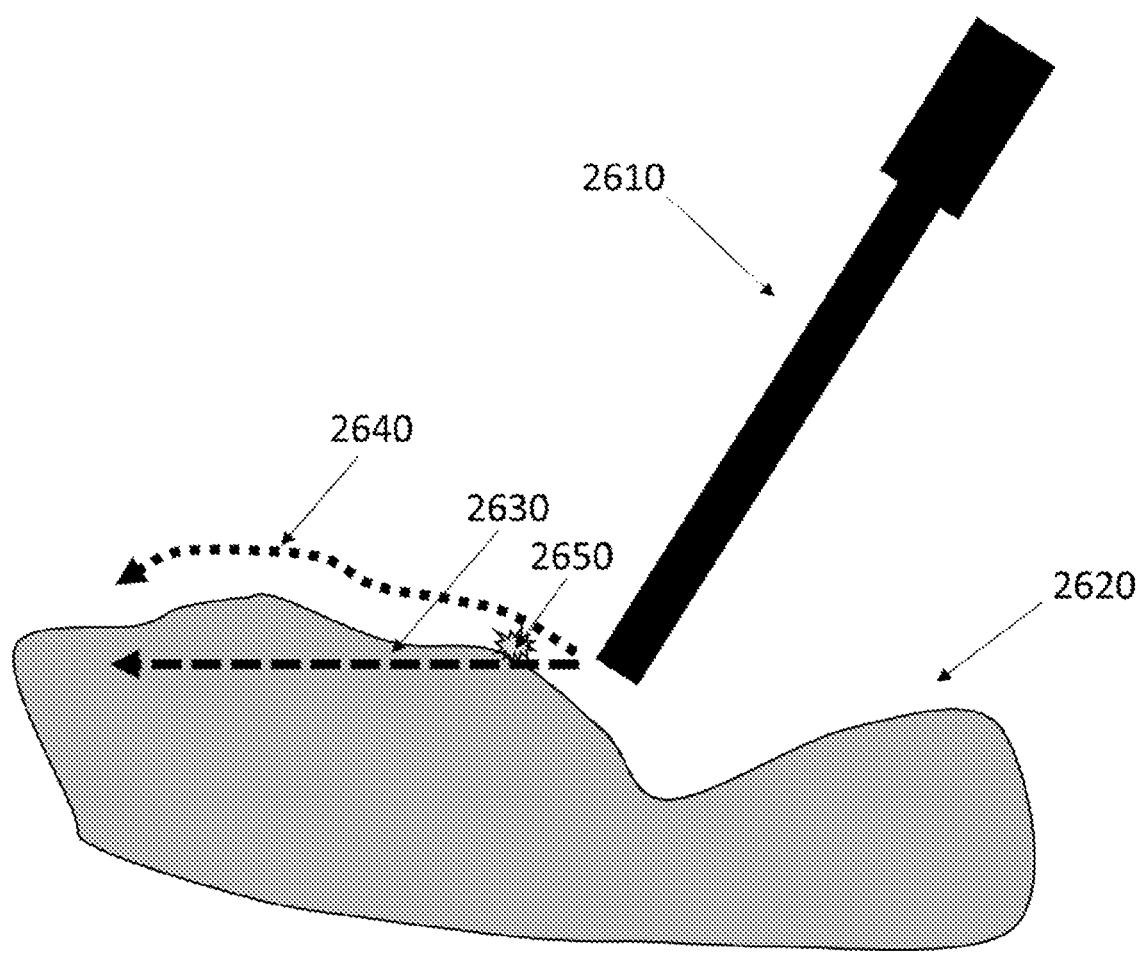
FIG. 19 schematically illustrates an embodiment of a smart response.

As illustrated in FIG. 18*b*, the system then directs and modifies the spatial position of the endoscope so that the tip of the tagged tool 1830 is at the location 1890. The tool 1730 has not been moved, nor has the center of the FOV been changed.

Example 19—Smart Response

Figure 20:
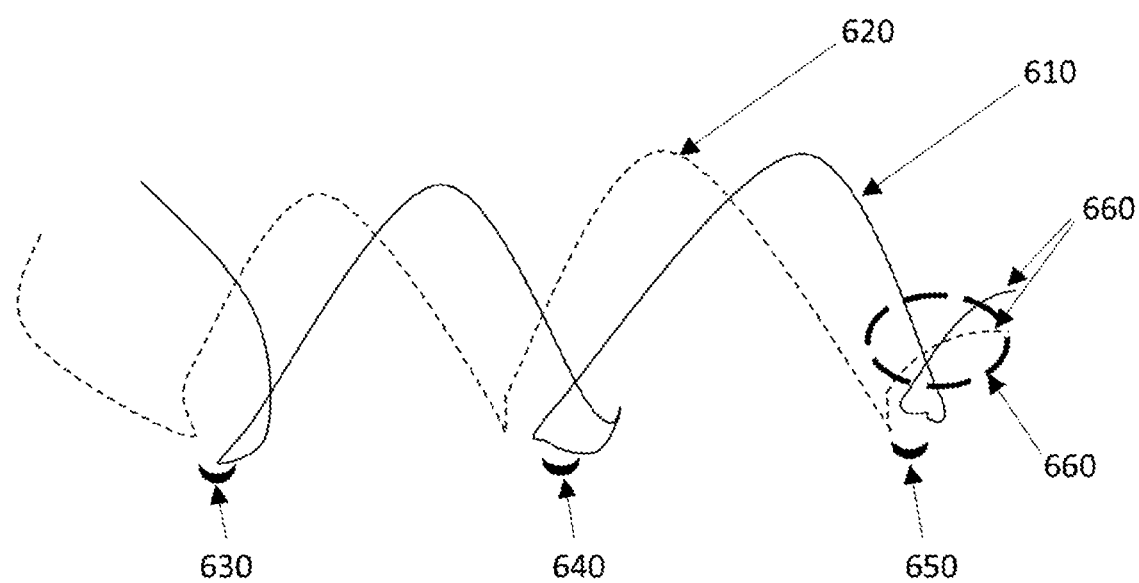
FIG. 20 schematically illustrates an embodiment of a smart command.

FIG. 20 shows an illustrative, not to scale, non-limiting example of a smart response. An endoscope (2610) is in proximity to an organ (2620) which it is viewing. The command "move left" is issued; the path that would be followed by a dumb response—moving left by a fised amount, is shown by the dashed arrow (2630). This path would cause the endoscope to collide with the organ at the point marked with the star (2650) and, if it were possible to continue the motion, the organ would be severely damaged.

In this exemplary smart response, the path (dotted line, 2640) is not a straight line. The tool moves upward to avoid the organ, then moves leftward. It maintains an approximately constant distance from the organ, so that it moves downward as it neats the end of the path.

Example 20—Smart Command

FIG. 20 shows an illustrative, non-limiting example of a response to a smart command. The command is "suture" and the response is tying knots to close an incision. The locations of the sutures are schematically illustrated by the arcs (2730, 2740, 2750). The movement of the tip of the forceps holding the needle (2710) and the movement of the tip of a second forceps (2720) are shown. For each suture, after the suture is complete, the tools move diagonally upward away from the suture location, before moving diagonally downward to the location of the next suture. After completion of the suturing (dashed circle, 2770), the movement of the graspers is nearly horizontal (2760), instead of a diagonal rise.

While various embodiments have been described above, it should be understood that they have been presented by way of example only, and not limitation. Thus, the breadth and scope of a preferred embodiment should not be limited by any of the above described exemplary embodiments, but should be defined only in accordance with the following claims and their equivalents.

We claim:

1. A vocally activated control system for controlling at least one robotically controlled surgical tool, said vocally activated control system comprises:
   at least one apparatus operable to spatially reposition a surgical tool, said apparatus comprising the surgical tool or a robotic arm having the surgical tool thereon;
   a voice sensor configured to detect at least one vocal command generated by at least one surgeon in said surgical setting;
   a signal transmitter operatively connected to said voice sensor, said transmitter is configured to convert said at least one vocal command into at least one transmittable vocal signal and transmit said at least one transmittable vocal signal;
   a processor operatively connected to said signal transmitter configured to receive said at least one transmittable vocal signal, said processor is configured to convert said at least one transmittable vocal signal to at least one predetermined set of operative instructions associated with at said least one apparatus, said at least one predetermined set of operative instructions comprising at least one instruction; and
   at least one controller operatively connected to said processor and said at least one apparatus; said at least one controller is configured to receive said predetermined set of operative instructions and to cause said at least one apparatus to operate accordingly;
   wherein said conversion of said transmittable vocal signal to said at least one predetermined set of operative instructions is performed to generate instructions according to a set of rules comprising a collision prevention rule and a no fly zone rule,
   said collision prevention rule configured to define a predetermined distance between said at least one surgical tool and an anatomical element within said surgical environment; said allowed movement is a movement which is in a range that is larger than said predetermined distance, and said restricted movement is a movement which is in a range that is smaller than said predetermined distance; said anatomical element being selected from a group consisting of tissue, organ, another surgical tool and any combination thereof;
   said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movement is a movement in which said at least one of said surgical tool is located substantially in at least one of said n 3D spatial positions, and said allowed movement is a movement in which the location of said at least one surgical tool is substantially different from said n 3D spatial positions.

2. The vocally activated control system according to claim 1, wherein at least one response to at least one said at least one vocal command is a smart response, said smart response being configured to take into account at least one feature of the an environment surrounding said robotically controlled surgical tool, said feature selected from a group consisting of a hazard or obstacle, an interference with a second surgical tool, an interference between two parts of an apparatus, interference between two apparatus, possibility of damage to a portion of a patient, and any combination thereof.

3. The vocally activated control system according to claim 1, wherein said at least one vocal command comprises at least one complex sentence; said voice sensor further comprising a context recognition unit configured to recognize said at least one vocal command from said complex sentence.

4. The vocally activated control system according to claim 1, wherein said vocal command can be unqualified or can comprise at least one qualifier, said at least one qualifier configured to modify at least one component of a response, and wherein at least one of the following:
   said qualifier is selected from a group consisting of an amount, a surgical tool, an apparatus, and any combination thereof; and
   said amount is either a fixed-term value or a fractional value.

5. The vocally activated control system according to claim 4, wherein said unqualified command is configured to comprise a predetermined qualifier or to continue a process until stopped.

6. The vocally activated control system according to claim 5, wherein at least one of the following:
   a. said predetermined qualifier is an amount, said amount being either a fixed-term value or a fractional value;
   b. said vocal command is configured to reversibly select a member of a group consisting of an apparatus, a surgical tool, at least a portion of a patient, and any combination thereof; a duration of said selection is selected from a group consisting of: for a predetermined time, or until reception of a change command;
   c. said vocal command is configured to change a member of a group consisting of: a predetermined amount; a value, a type of value and any combination thereof.

7. The vocally activated control system according to claim 1, wherein said system is configured to provide an alert of said restricted movement of said at least one surgical tool.

8. The vocally activated control system according to claim 1, wherein said allowed movement is permitted by said controller and said restricted movement is denied by said controller.

9. The vocally activated control system according to claim 1, wherein at least one of the following: (a) said system additionally comprises an endoscope; said endoscope is configured to provide real-time image of said surgical environment; (b) at least one of said surgical tools is an endoscope configured to provide real-time image of said surgical environment.

10. The vocally activated control system according to claim 1, additionally comprising at least one location estimator, wherein said at least one location estimator comprises at least one endoscope configured to acquire real-time images of said surgical environment within said human body; and at least one surgical instrument spatial location software configured to receive said real-time images of said surgical environment and to estimate a 3D spatial position of said at least one surgical tool.

11. The vocally activated control system of claim 10, wherein at least one of the following:
  a. said at least one location estimator comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element;
  b. said at least one location estimator is an interface subsystem between a surgeon and the at least one surgical tool, the interface subsystem comprises:
    i. at least one array comprising N regular or pattern light sources, where N is a positive integer;
    ii. at least one array comprising M cameras, each of the M cameras, where M is a positive integer;
    iii. optional optical markers and means for attaching the optical marker to the at least one surgical tool; and;
    iv. a computerized algorithm operable via the controller, the computerized algorithm configured to record images received by each camera of each of the M cameras and to calculate therefrom the position of each of the tools, and further configured to provide automatically the results of the calculation to the human operator of the interface.

12. A method of controlling at least one robotically controlled surgical tool via vocal activation, said method comprises steps of:
  a. providing a vocally activated control system comprising:
    i. a voice sensor configured to detect at least one vocal command generated by at least one surgeon in said surgical setting;
    ii. a signal transmitter operatively connected to said voice sensor, said transmitter is configured to convert said at least one vocal command into at least one transmittable vocal signal and transmit said at least one transmittable vocal signal;
    iii. a processor operatively connected to said signal transmitter configured to receive said at least one digital transmittable vocal signal, said processor is configured to convert said at least one transmittable vocal signal to at least one predetermined set of operative instructions associated with said at least one apparatus, said at least one predetermined set of operative instructions comprising at least one instruction; and,
    iv. at least one controller operatively connected to said processor and said at least one apparatus; said at least one controller is configured to receive said predetermined set of operative instructions and to cause said at least one apparatus to operate accordingly;
  b. detecting said at least one vocal command generated by said at least one surgeon in said surgical setting via said voice sensor;
  c. converting said at least one vocal command into a transmittable vocal signal via said signal transmitter;
  d. transmitting said transmittable vocal signal using said signal transmitter;
  e. receiving said transmittable vocal signal through said processor operatively connected to said transmitter;
  f. converting said transmittable vocal signal to said at least one predetermined set of operative instructions associated with said at least one robotically controlled surgical tool via said processor, to generate instructions according to a predetermined set of rules, said at least one predetermined set of rules comprising at least one rule selected from a group consisting of: no fly zone rule, and collision prevention rule, allowed movement being movements of said surgical tool permitted by said controller and said restricted movement being movements of said surgical tool denied by said controller according to said predetermined set of rules;
  g. receiving said predetermined set of instructions by said at least one controller operatively connected to said processor and said at least one apparatus;
  h. operating said at least one robotically controlled surgical tool according to said predetermined set of instructions using said at least one control mean.

\* \* \* \* \*